United States Patent
Horiguchi et al.

(10) Patent No.: US 7,085,046 B2
(45) Date of Patent: Aug. 1, 2006

(54) MICROSCOPE FOR OPERATION

(75) Inventors: Masayuki Horiguchi, Nagoya (JP);
Nobuaki Kitajima, Tokyo (JP);
Noriaki Kanazawa, Tokyo (JP)

(73) Assignee: Kabushiki Kaisha TOPCON, Tokyo (JP)

(*) Notice: Subject to any disclaimer, the term of this patent is extended or adjusted under 35 U.S.C. 154(b) by 0 days.

(21) Appl. No.: 11/195,939

(22) Filed: Aug. 3, 2005

(65) Prior Publication Data
US 2005/0264876 A1    Dec. 1, 2005

Related U.S. Application Data

(62) Division of application No. 10/167,701, filed on Jun. 12, 2002, now Pat. No. 6,943,942.

(30) Foreign Application Priority Data

Jun. 13, 2001  (JP)  ............................. 2001-178299
Mar. 26, 2002  (JP)  .............................. 2002-85092

(51) Int. Cl.
G02B 21/00  (2006.01)

(52) U.S. Cl. ...................... 359/381; 359/368; 359/384
(58) Field of Classification Search ................ 359/368, 359/380–384, 391–393; 351/200–246
See application file for complete search history.

(56) References Cited

U.S. PATENT DOCUMENTS

| | | | | |
|---|---|---|---|---|
| 5,270,855 A | * | 12/1993 | Hasegawa | 359/368 |
| 5,526,074 A | * | 6/1996 | Volk | 351/219 |
| 6,072,622 A | * | 6/2000 | Biber | 359/368 |
| 6,142,630 A | * | 11/2000 | Koester | 351/219 |
| 6,212,006 B1 | * | 4/2001 | Reiner | 359/388 |
| 6,788,455 B1 | * | 9/2004 | Kirchhuebel et al. | 359/381 |
| 6,937,390 B1 | * | 8/2005 | Akiyama et al. | 359/381 |
| 6,943,942 B1 | * | 9/2005 | Horiguchi et al. | 359/381 |

FOREIGN PATENT DOCUMENTS

DE   94 15 219   * 1/1995
WO   WO 91/15150  * 10/1991

* cited by examiner

Primary Examiner—Thong Q Nguyen
(74) Attorney, Agent, or Firm—Chapman and Cutler LLP

(57) ABSTRACT

Disclosed is a microscope for operation. This microscope for operation comprises a front lens 15 disposed between an eye 8 to be operated and an objective 14. The front lens collects an illuminating light P to guide the collected light within the eye for illuminating an interior of the eye. An operator performs an operation within the eye through an eyepiece 39. A refracting power of the front lens 15 is within a range of 30 D to 50 D.

3 Claims, 29 Drawing Sheets

MICROSCOPE FOR OPERATION

CROSS-REFERENCE TO RELATED APPLICATIONS

This application is a division of U.S. application Ser. No. 10/167,701, filed Jun. 12, 2002, now U.S. Pat. No. 6,943,942.

BACKGROUND OF THE INVENTION

1. Field of the Invention

The present invention relates to a microscope for operation in which an operation within an operated eye is performed by watching an eyepiece in a state of introducing collected illuminating light into the operated eye and illuminating within the operated eye with the collected illuminating light through a front lens which is disposed between the operated eye and an anterior focus position of an objective.

2. Description of Prior Art

Hitherto, there is known a microscope for operation, for example, a stereo microscope apparatus for operation having a configuration as shown in FIG. 1.

In FIG. 1, numeral 1 denotes a pillar, numeral 2 a first arm, numeral 3 a second arm, numeral 4 a X-Y micromotion device, numeral 5 an operation microscope (referred to, also, as a microscope device), numeral 6 an assistant microscope, numeral 7 a foot switch, and numeral 8 an eye or operated eye. Conventionally, when an operation for the operated eye 8 is performed, an operator causes a contact lens 9 to contact with cornea C of the operated eye 8 as shown in FIG. 2 in an enlarged state.

Next, the operator inserts a light guide 10 for illumination within the eye into the eye and performs the operation by means of an operation instrument 11 such as a cutter, watching an eyepiece in the microscope. Note that in FIG. 2, numeral 12 is crystalline lens of the eye, numeral 13 is vitreous cavity of the eye.

In the conventional microscope for operation, the operator must perform the operation with having the light guide 10 at one hand. Accordingly, it is very difficult to perform a fine operation. So, it is desirable to perform an operation with the operator having operating instruments 11 at both hands (for example, a pair of tweezers at one hand and a cutter at the other hand).

As a result, as shown in FIG. 3, a front lens 15 may be disposed in a front portion of the operated eye 8 between an objective 14 provided in an objective body tube of the microscope and the operated eye 8. An inside of the operated eye 8 is, also, illuminated through the front lens 15.

The microscope for operation having such a construction is preferable to the operator.

However, if the front lens 15 is disposed between the objective 14 and operated eye 8, the following problems are considered.

For example, when a focus distance F1 of the front lens 15 is too long, since a distance from the eyepiece of the microscope to the operated eye 8 is long, it is difficult for the operator to perform the operation.

On the contrary, when the focus distance F of the front lens 15 is too short, the front lens tends to contact with the operated eye 8.

When the operated eye 8 is, also, washed by physiological saline solution during an operation, there is a problem that the saline solution adheres to the front lens 15 by dispersion of the saline solution.

Furthermore, if the diameter of the front lens 15 is too large, a space between the operation instruments 11 is large by interference of the front lens. In this case, there is an inconvenience that it is difficult to perform an operation with having the operation instruments 11 at both hands. Note that reference numeral 16 denotes one or more inserting parts for inserting the operation instrument(s) 11 into the eye through the part.

SUMMARY OF THE INVENTION

The present invention is made in view of circumstances described above. It is an object of the present invention to provide a microscope for operation in which an operation can be preferably performed by illuminating an inside of the operated eye with illuminating means of the microscope and having operation instruments at the both hands in a state of disposing a front lens in a front portion of the operated eye.

A microscope for operation according to a first aspect of the present invention is characterized in that it comprises an objective including an anterior focus position, a front lens disposed between the anterior focus position of the objective and an eye to be operated, an illuminating light for illuminating within the operated eye, and an eyepiece. The front lens collects the illuminating light and guides the collected light in the operated eye to illuminate the interior of the eye, and thereby the microscope is capable of performing an operation within the eye through the eyepiece. A refracting power of the front lens is within a range of 30 D to 50 D.

It is desirable that in the microscope, if a refracting power is D of the front lens and a diameter of the front lens is $\Phi$, the diameter is selected so that $\Phi \times D$ is within a range of 0.8 to 1.0.

A microscope for operation according to a second aspect of the present invention is characterized in that it comprises a front lens disposed between an operated eye and an anterior focus position of an objective, a movable holding arm on which the front lens is provided, an objective body tube for holding the objective, a slide member on which the objective body tube is mounted for causing said objective body tube to move upwardly and downwardly along an optical axis, and a body portion for holding slidably the slide member.

A base portion of the holding arm is provided on the body portion.

It is desirable that in the microscope for operation the front lens is micro-motioned upwardly and downwardly in accordance with upward and downward movement of said objective body tube.

A microscope for operation according to a third aspect of the present invention is characterized in that it comprises an objective having an anterior focus position, a front lens disposed between an eye to be operated and the anterior focus position of the objective, a holding arm on which the front lens is provided, and a prism provided rotatably on said holding arm for observing a peripheral portion of fundus of the eye.

A microscope for operation according to a fourth aspect of the present invention is characterized in that it comprises an objective body tube, an objective provided in the objective body tube to opposite to an eye to be operated, a front lens disposed between the objective and operated eye to collect illuminating light and to guide the collected light within said eye for illuminating the interior of the eye, and a holding arm provided movably on the objective body tube for holding the front lens.

The holding arm positions the front lens to move it in and out of an optical path between the operated eye and the objective.

It is desirable that in the microscope for operation, a refracting power of the front lens is within a range of 30 D to 50 D.

It is, also, desirable that a diameter Φ of the front lens is selected that if a refracting power of the front lens is D, Φ×D is within 0.8 to 1.0.

It is, further, desirable that the microscope for operation comprises a rough-motion mechanism and a micro-motion mechanism for causing the holding arm to move upwardly and downwardly.

According to the first to fourth aspects of the present invention, it is able to perform an operation having the operation instruments at both hands with disposing the front lens in a front of the operated eye and illuminating the interior of the eye.

With the micro-motion and rough-motion mechanisms for moving upwardly and downwardly the holding arm, it is able to observe the interior of the eye in a focused state throughout a wide range from the fundus to the neighborhood of crystalline body.

In addition, the microscope for operation has a configuration that a loupe holding mechanism is provided on the holding arm. The loupe holding mechanism holds a convex lens to observe the inserting part of the operation instrument to the operated eye to move the convex lens in and out of the optical path between the front lens and the objective.

With such configuration, it is able to insert the convex lens in the optical path between the front lens and objective and to observe the inserting part for the operation instrument in a focused state. The convex lens can be evacuated out of the optical path when the interior of the eye is observed. The inserting part can be observed in a stable state.

The convex lens is movable upwardly and downwardly relative to the holding arm to enable observation of the inserting part in a focused state even though the other portion than the fundus is being observed.

A microscope for operation according to a fifth aspect of the present invention is characterized in that it comprises an illuminating optical system for illuminating an illuminating light toward an eye to be operated, an objective body tube, an objective provided on the objective body tube to opposite to the eye, a pair of observing optical systems disposed at the opposite sides of an optical axis of the objective for observing the operated eye, and a front lens disposed between the objective and the operated eye to collect the illuminating light and to guide the collected light in an interior of the eye for illuminating the interior of the eye.

The illuminating optical system is provided with a slit plate having a slit hole for converting the illuminating light into a slit illuminating light. The slit hole extends in a direction vertical to an optical axis of the illuminating optical system.

An image of said slit hole focused on the fundus of the eye is parallel to a plane including both axes of the observing optical systems. The slit plate is movable in a direction vertical to the optical axis of the illuminating optical system for moving said slit illuminating light to approach to and separate from the optical axis of the objective.

According to the fifth aspect of the present invention, the reflected light on a back surface of the crystalline body is not entered into the observing optical system to prevent a glare from occurring.

BRIEF DESCRIPTION OF THE DRAWINGS

The above and other objects, structures and advantageous of the present invention will become more apparent by the following description with reference to the accompanying drawings in which.

DETAILED DESCRIPTION OF THE PREFERRED EMBODIMENTS

Embodiment 1

Figure 1:
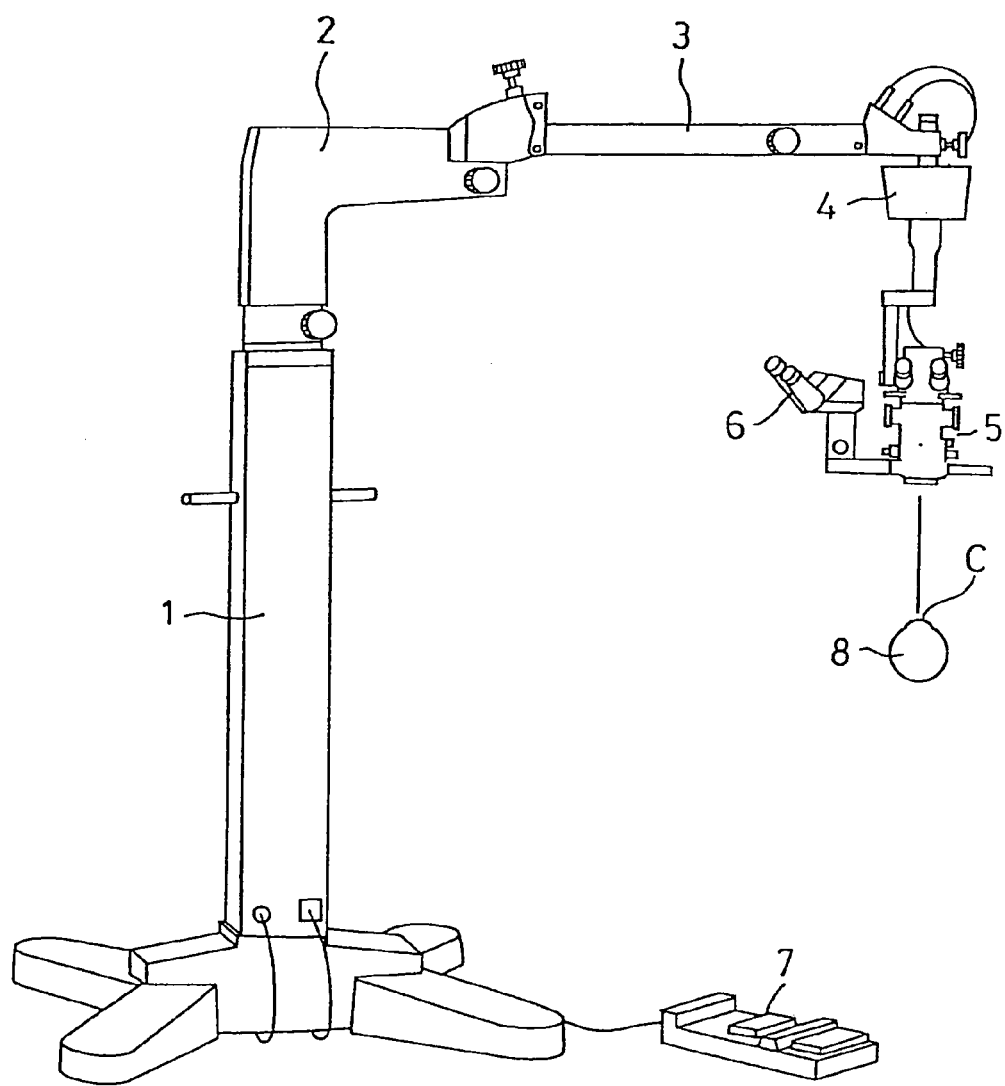
FIG. 1 is a view showing a schematic construction of a conventional microscope for operation.
Figure 2:
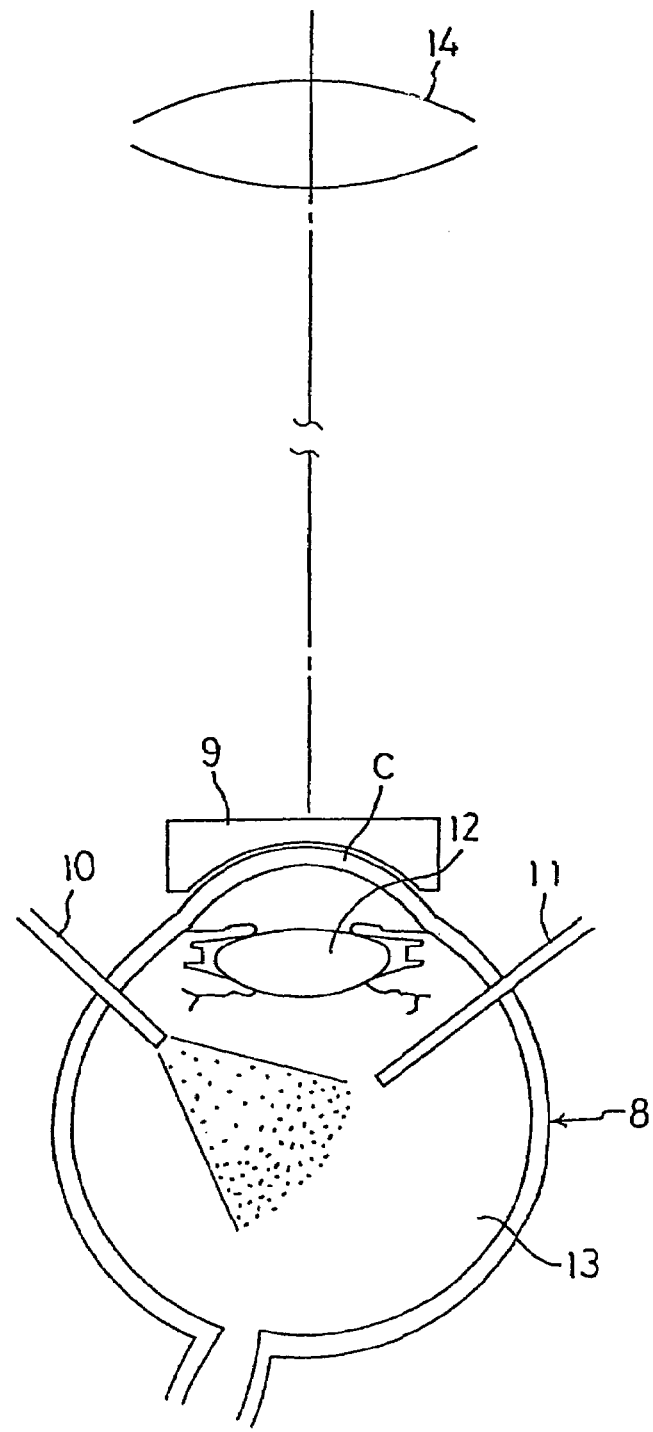
FIG. 2 is a view showing one example in case of performing an operation within an eye with having a light guide at one hand and having an operation instrument at the other hand.
Figure 3:
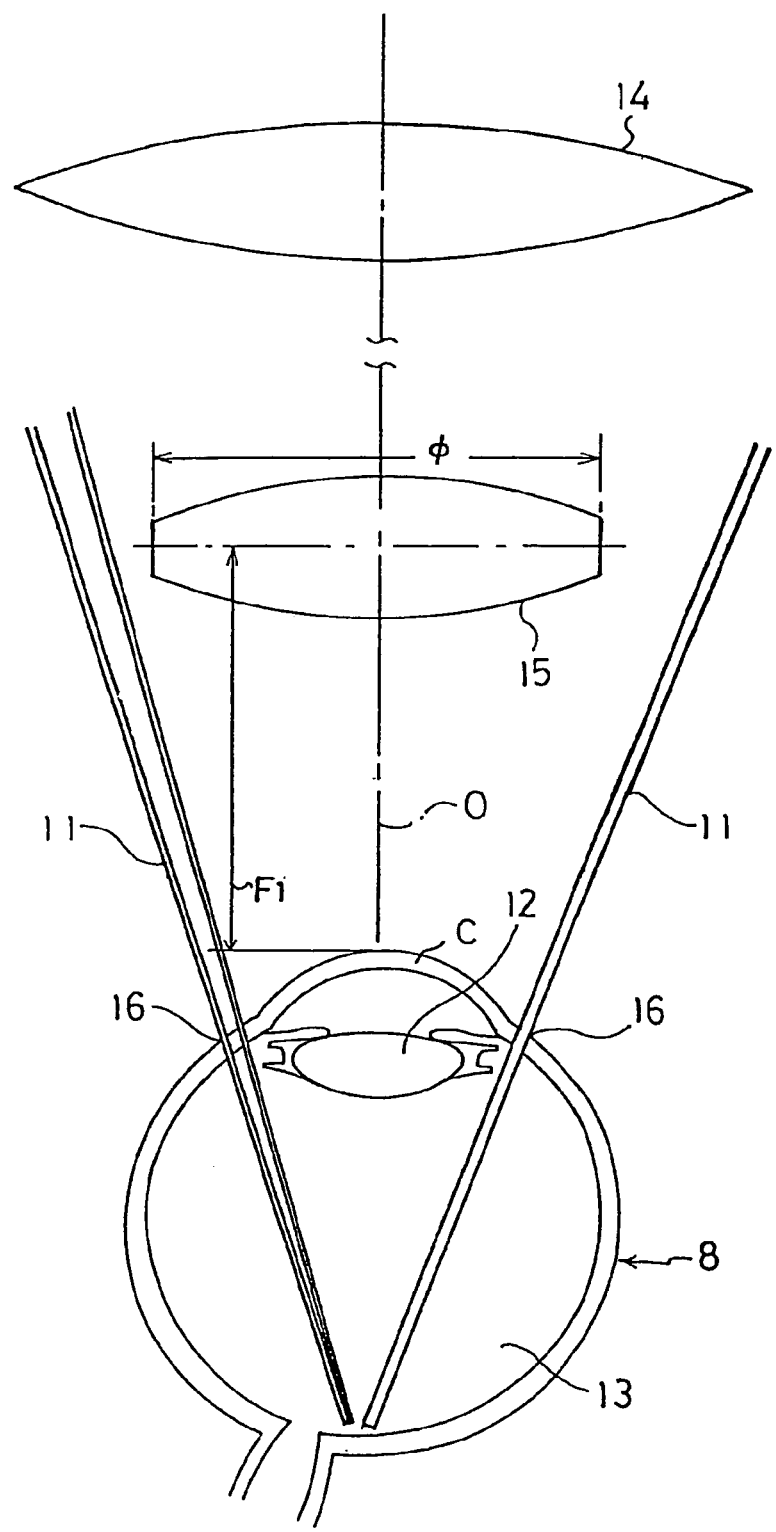
FIG. 3 is a view showing one example in case of performing the operation within the eye with having the operation instrument at both hands.
Figure 4:
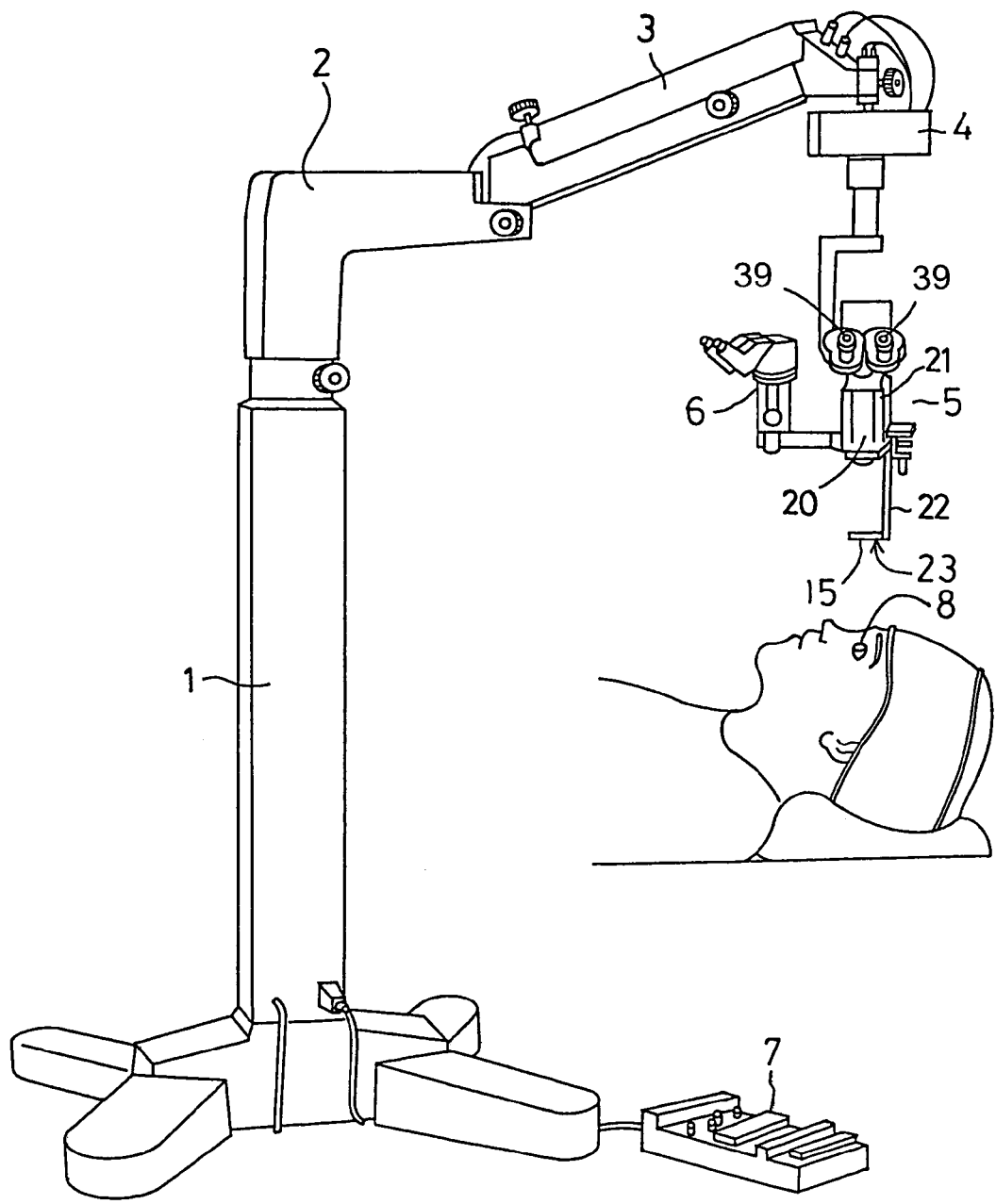
FIG. 4 is a view showing a schematic construction of a microscope for operation according to the present invention.

In FIG. 4, the same numerals are annexed to the identical elements with that of the prior art microscope described in FIG. 1.

A microscope 5 for an operator comprises an objective body tube 20, an inverter portion 21 and a holding arm 22 as shown in FIG. 4.

Figure 5:
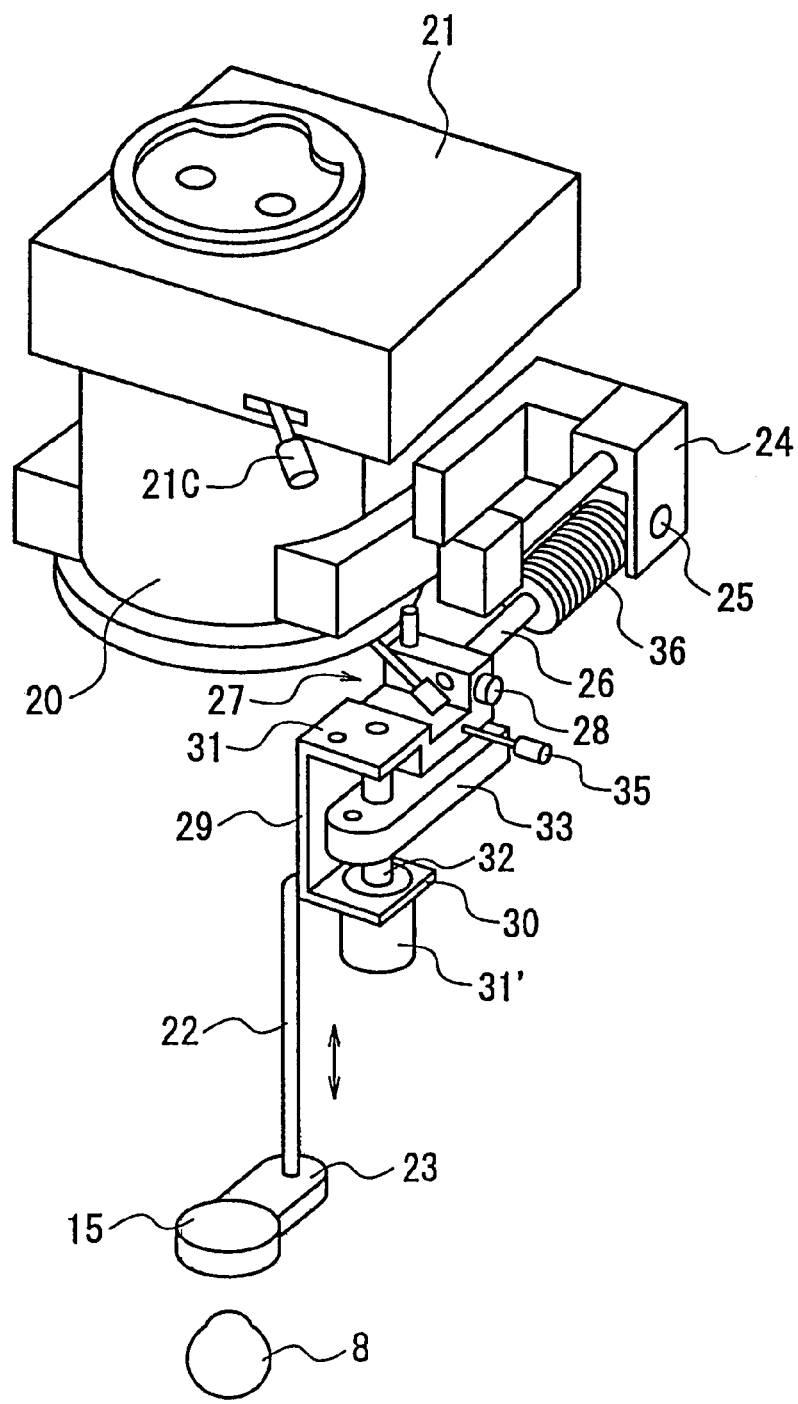
FIG. 5 is a partial enlarged perspective view showing an objective body tube as shown in FIG. 4.

FIG. 5 is a partially enlarged view of the objective body tube 20.

Figure 6A:
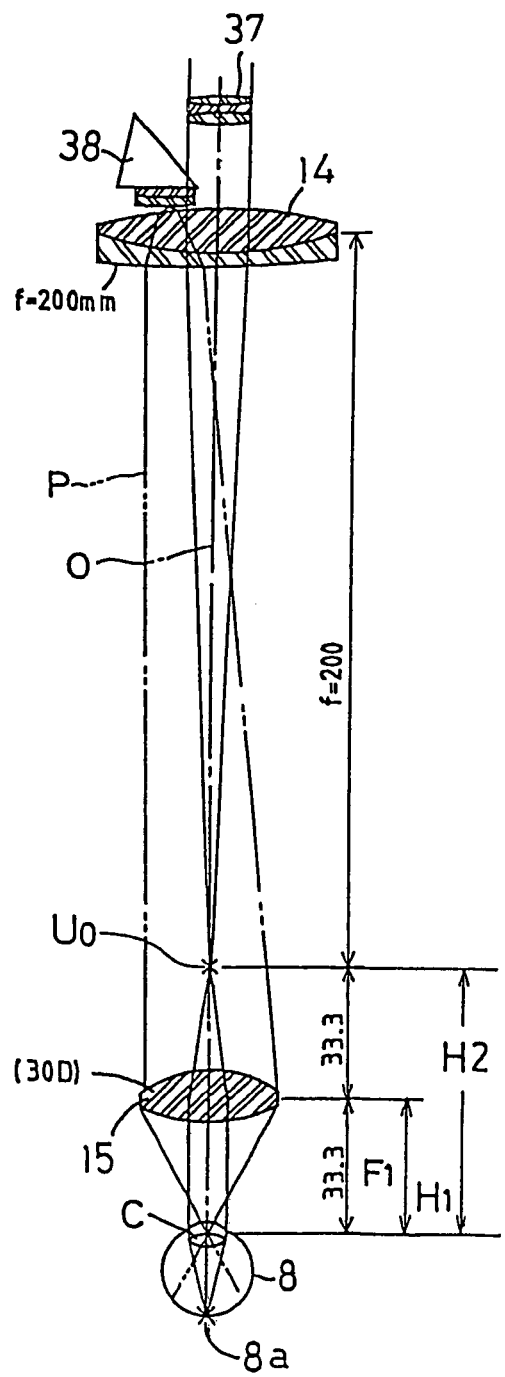
FIG. 6(a) is an optical view showing an optical disposed relationship of an objective provided in the objective body tube and a front lens, wherein the front lens has a focus distance F of 33.3 mm and a diameter Φ of 33.3 mm.
Figure 6B:
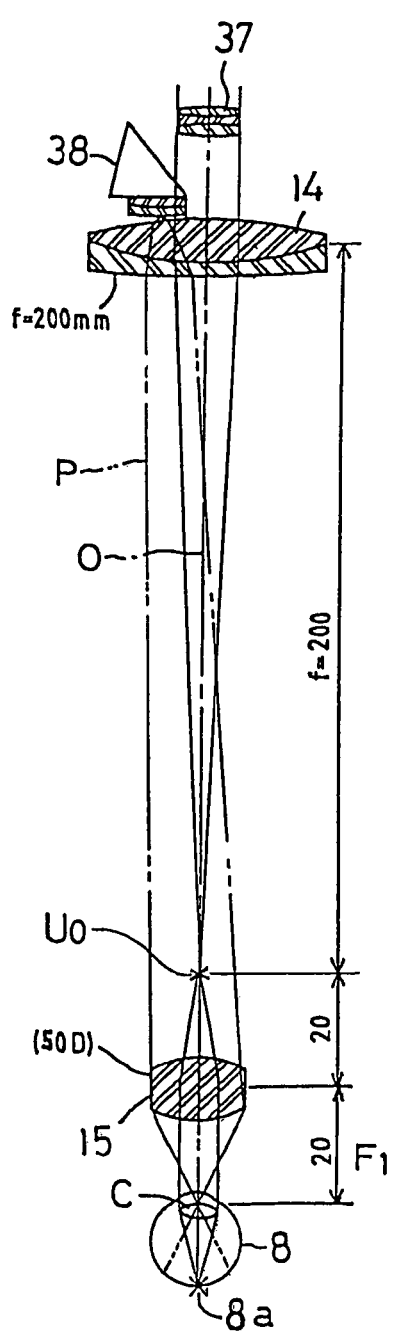
FIG. 6(b) is an optical view showing an optical disposed relationship of the objective end front lens, wherein the front lens has a focus distance F of 20 mm and a diameter Φ of 20 mm.
Figure 7:
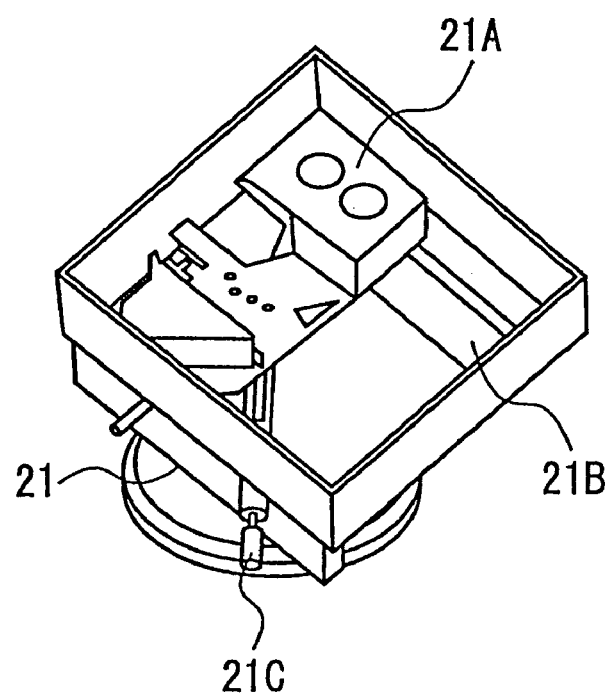
FIG. 7 is a view showing schematically an inner construction as shown in FIG. 4.

The objective body tube 20 is provided with an objective 14 as shown in FIG. 6. The inverter portion 21 is provided with a lens unit 21A for converting an inverted image whose up and down, right and left are visible inversely into an erect image, as shown in FIG. 7.

The lens unit 21A is reciprocated along slide rails 21B and is inserted into and moved out of an optical path of the objective 14 by a changing lever 21C.

A leading end of the holding arm 22 is provided with a holding plate 23 on which a front lens 15 is provided. The objective body tube 20 is provided with a fixed bracket 24 on which a turned rod 25 is mounted.

A supporting shaft 26 is mounted on the turned rod 25. A supporting bracket 27 is mounted on the supporting shaft 26 by means of a fixed screw 28. The supporting bracket 27 has a holding frame portion 29 which has a lower plate 30 and an upper plate 31.

A micro-motion adjusting knob 31' is mounted on the lower plate 30. An upwardly and downwardly extending rotated screw 32 is provided between the lower and upper plates 30 and 31. The rotated screw 32 is provided with a movable plate 33.

The holding arm 22 is bent in a crank shape. The other end portion of the holding arm 22 is inserted into a through hole which is formed in the supporting bracket 27.

Figure 8:
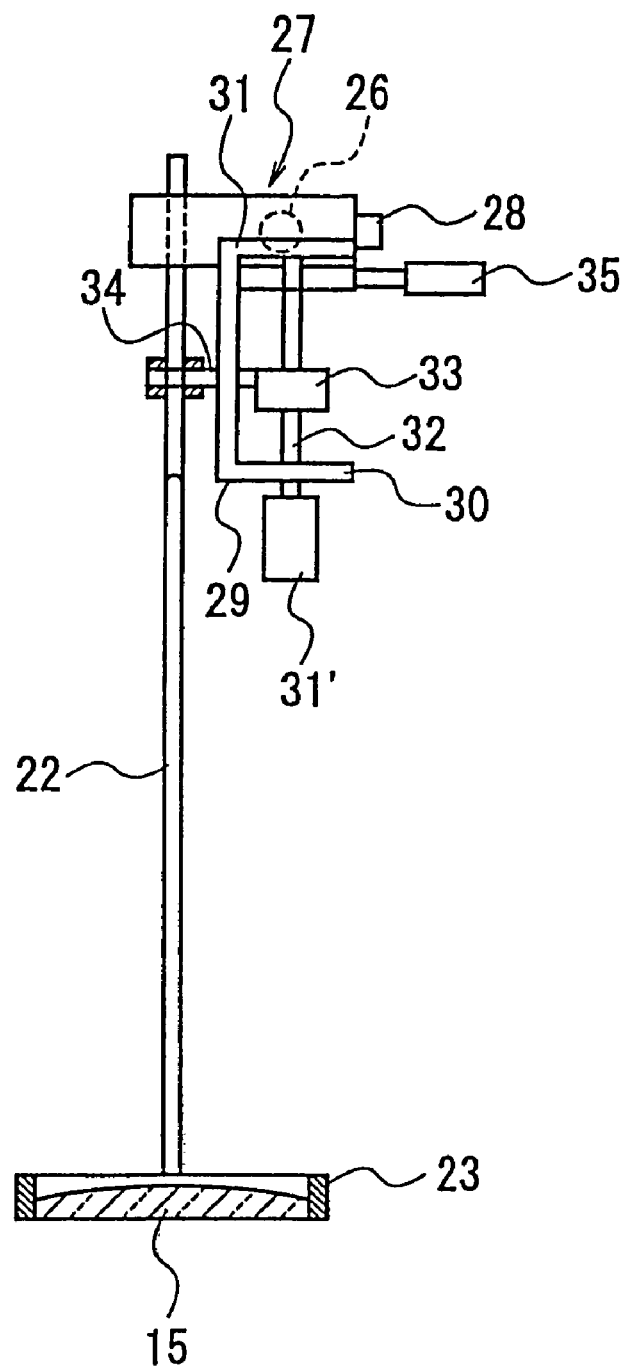
FIG. 8 is a front view showing a mounting relationship of the objective body tube and a holding arm as shown in FIG. 5.
Figure 9:
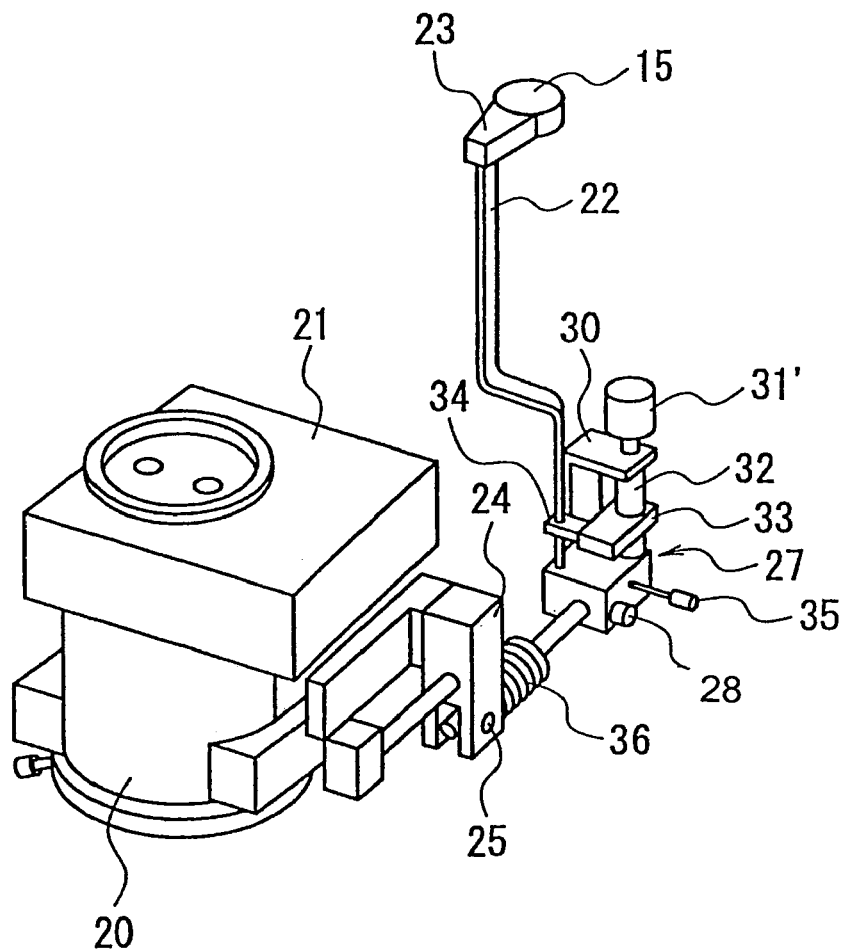
FIG. 9 is an explanatory view showing the front lens in an evacuated state as shown in FIG. 4.

As shown in FIG. 8, the movable plate 33 has an arm portion 34 which is engaged with the holding arm 22. The movable plate 33 is movable upwardly and downwardly by adjusting the micro-motion adjusting knob 31' to adjust a micro-motion for the holding arm 22 in upward and downward directions.

The supporting bracket is, also, provided with a turned lever 35. The holding arm 22 can be turned about the turned rod 25 by means of the turned lever 35. For example, when the operator wants to observe a front eye portion of the operated eye 8 and an operation is performed by use of the contact lens 9, the holding arm 22 is moved into a standing-up state and can be evacuated from a forward portion of the operated eye 8.

Note that reference numeral 36 denotes a coil spring for holding the holding arm 22 in the standing up and use states.

Provided in the objective body tube 20 are a pair of zoom lenses 37 which are disposed in symmetrical positions with respect to the optical axis O of the objective 14 and an illuminating prism 38 which is biased from the optical axis O.

An anterior focus distance f of the objective 14 is, for example, 200 mm in the embodiment. The front lens has a focus distance F of more than 20 mm and less than 33.3 mm, in other words, has a refracting power (inverse number of the focus distance F) in a range of 30 D (diopters) to 50 D.

The front lens 15 is disposed at a position of distance H1 from the apex of the cornea as shown in FIG. 6(*a*). A posterior focus position of the front lens 15 is positioned at a point of distance H2 from the apex of the cornea C.

Illuminating light P is emitted from a light power (not shown) and is formed into a diffusion beam by means of the objective 14 as shown in FIG. 6. Thereafter, the illuminating light P is formed into a convergent beam by the front lens 15.

The convergent beam is guided in the interior of the eye through the cornea of the operated eye 8 to illuminate the interior of the eye.

Reflected light reflected on the interior of the eye once forms an air image in the near of the anterior focus position u0 of the objective 14 through the front lens 15.

Thereafter, the reflected light is guided to the eyepiece 39 shown in FIG. 4 through the objective 14, zoom lenses 37, and inverter portion 21 to thus enable the operator to observe the interior of the eye with watching the eyepiece 39.

FIGS. 6(*a*) and (*b*) show a relative position relationship of the objective 14, front lens 15, and operated eye 8 in observing the retina 8*a* in a state of coinciding the posterior focus position of the front lens 15 with the anterior focus position u0 of the objective 14 and focusing on the retina 8*a* of the operated eye 8.

Figure 10A:
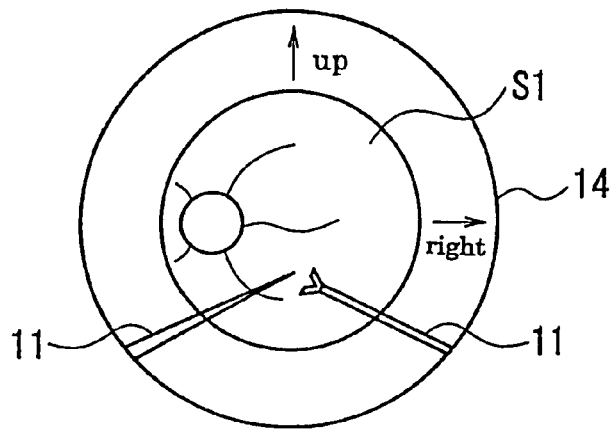
FIG. 10(a) is an explanatory view showing a state of an image of an eye to be operated through an eyepiece when the front lens is disposed or is not disposed in a forward portion of the operated eye; wherein the forward portion of the operated eye by contacting a contact lens with the operated eye is observed.

When observing the interior of the eye through the eyepiece 39 with contact between the contact lens 9 and the operated eye 8, the erect image S1 of the fundus can be observed as shown in FIG. 10(a). When the front lens 15 is disposed at a front portion of the operated eye 8 and the interior of the eye is observed through the front lens 15, the inverted image S2 whose up and down and right and left are inverse can be observed as shown in FIG. 10(b).

Figure 10B:
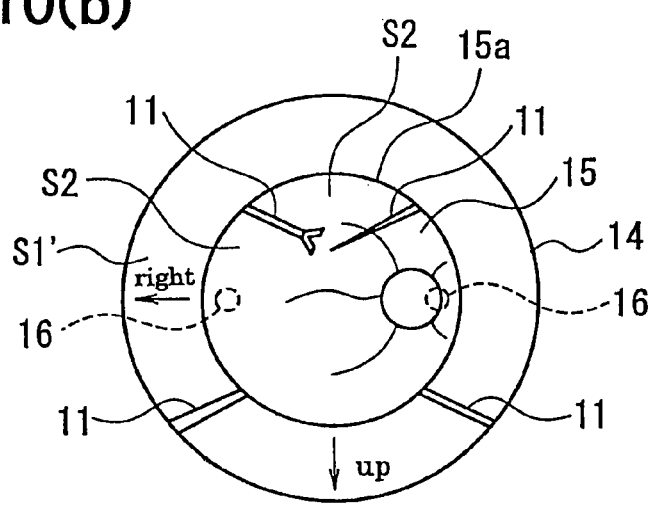
FIG. 10(b) is a view similar to FIG. 10(a) showing how to view an image of the eye when the front lens is disposed in the front portion of the operated eye.
Figure 10C:
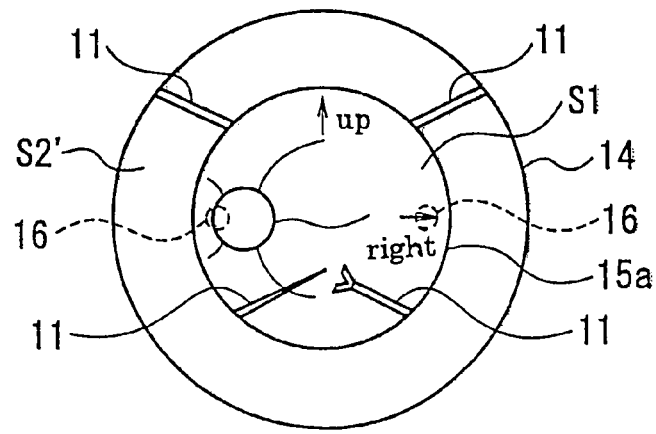
FIG. 10(c) is a view similar to FIG. 10(a) showing how to view an image of the operated eye when a lens unit is used.

Accordingly, as the lens unit 21A is inserted into the optical path of the objective 14 by operating the changing lever 21C the erect image S1 can be observed through the front lens 15 as shown in FIG. 10(c).

Reference numeral 15a denotes an edge of the front lens 15. An image of the operated eye 8 can be viewed at the outside of the front lens 15 through the objective 14.

In FIG. 10(b), the erect image S1' of the front portion of the operated eye 8 is observed. In FIG. 10(c), the inverted image S2' of the front portion of the operated eye 8 is observed.

Note that in the embodiment, FIG. 10 shows how to view a back end portion of the operation instrument 11 which can be viewed through the objective 14 at the outside of the front lens 15.

Reasons that the refracting power (inverse number of the focus distance F) of the front lens 15 is more than 30 D are as follows.

Namely, if the refracting power of the front lens 15 is below 30 D, a distance between the operated eye 8 and objective 14 becomes long.

In other words, it becomes difficult to perform the operation since a distance between the operated eye 8 and eyepiece 39 is too long.

Further, reasons that the refracting power of the front lens 15 is less than 50 D are as follows.

If the refracting power of the front lens 15 is over 50 D, the distance between the operated eye 8 and front lens 15 is too short. As a result, there is increased possibility of contacting the front lens 15 with the operated eye 8. Also, in operation, if the physiological saline solution is poured in the operated eye 8 to wash the operated eye, the saline solution is scattered to adhere to the front lens 15, thus causing the observation to be difficult.

Further, a diameter Φ of the front lens 15 is selected such that if a refracting power is D, Φ×D is within 0.8 to 1.0.

This is for the following reason.

If the diameter Φ of the front lens 15 is too small, a viewing field becomes narrow. On the contrary, if the diameter Φ of the front lens 15 is too large, a space between the operation instrument 11 and front lens 15 becomes narrow.

Accordingly, it is not able to reach the operation instrument(s) 11 to an operated part or painful part on the fundus in performing the operation with having the operation instrument 11 at both hands.

As described above, when the refracting power of the front lens 15 is set in a range of 30 D to 50 D and the diameter Φ of the front lens 15 is selected such that Φ×D is within a range of 0.8 to 1.0, it becomes very easy to perform the operation with having the instruments 11 at both hands and illuminating the inside of the eye by disposing the front lens 15 in the front portion of the operated eye 8.

(Modification)

Figure 11:
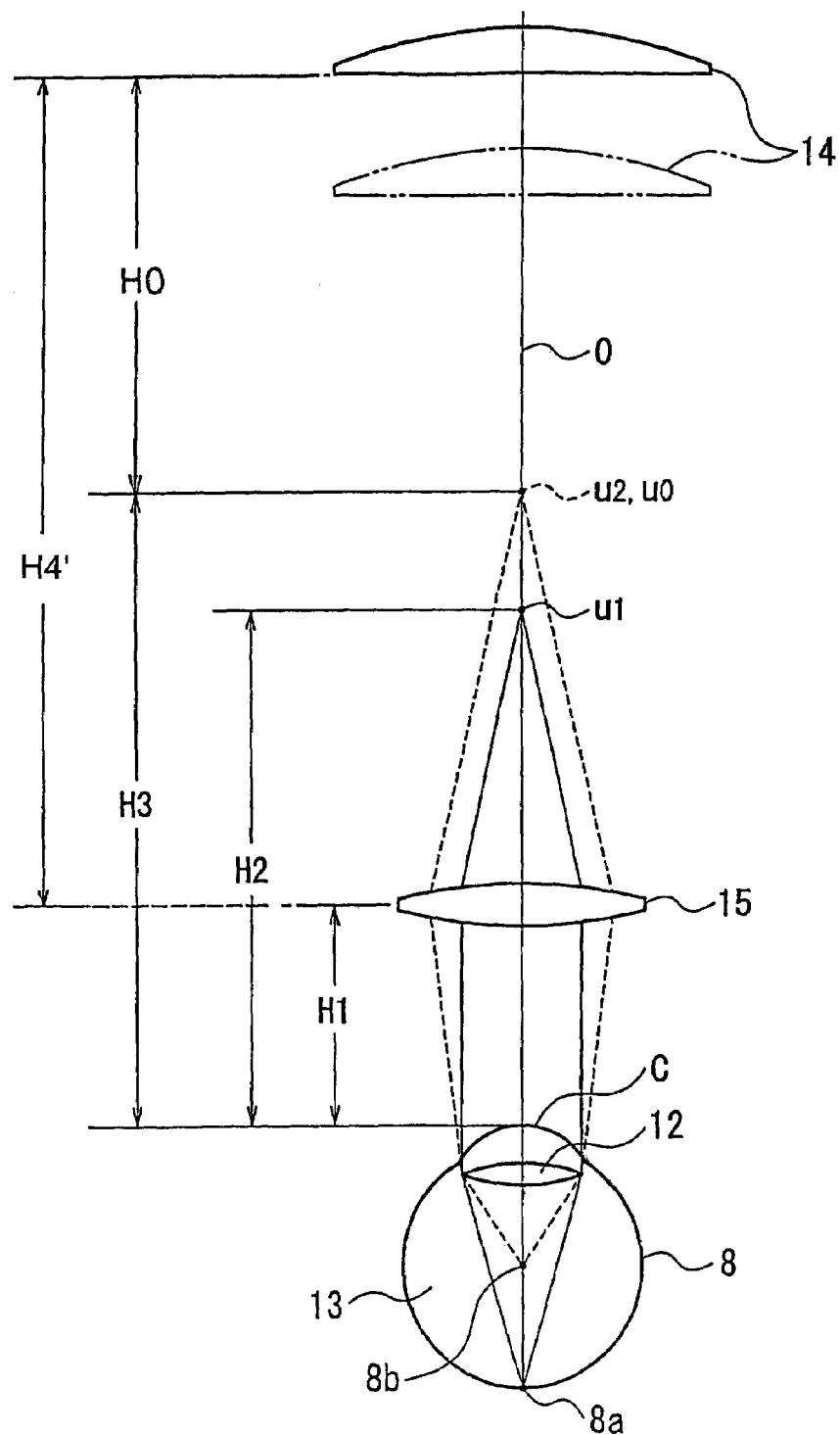
FIG. 11 is a pattern diagram for explaining a focused position of a part of vitreous body different from retina of the operated eye in a modified example of an embodiment 1.

As shown schematically in FIG. 11, when the front lens 15 is disposed in a position of a distance H1 from the apex of the cornea C of the operated eye 8, the image of the retina 8a is focused on a position u1 of a distance H2 from the apex of the cornea C of the operated eye 8.

Figure 12:
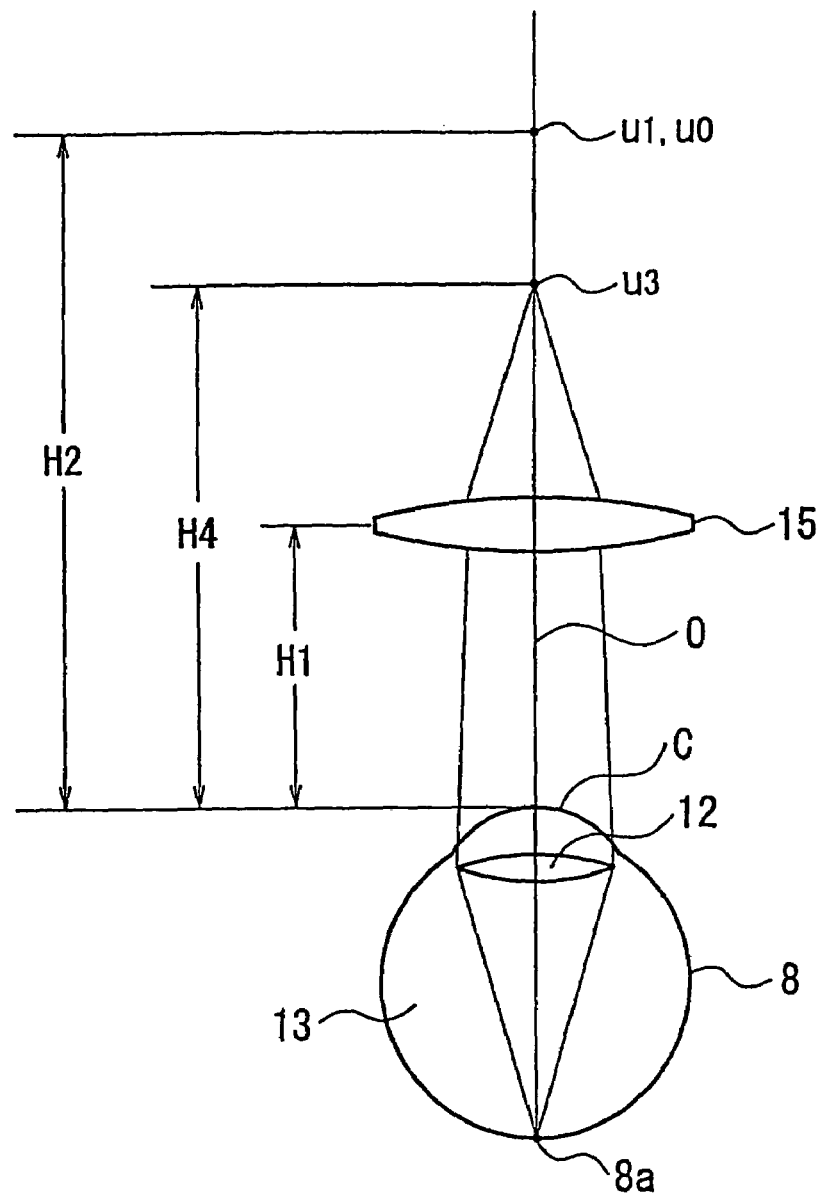
FIG. 12 is a pattern diagram for explaining a focused position of the retina of the operated eye when gas or air is filled in the eye by removing the vitreous body of the operated eye in a modified example of the embodiment 1.

On the other hand, for example, an image of a portion 8b of the vitreous body is focused on a position u2 of a distance H3 from the apex of the cornea C. When an operation for the vitreous body is performed, injection of gas into the operated eye 8 may be effected with removing the vitreous body. In such case, as shown in FIG. 12, the image of the retina 8a is focused on a position u3 of a distance H4 from the apex of the cornea C of the operated eye 8.

It is required to perform the operation by observing such operated part when performing the operation. However, it is not able to view the part in a focused state by only operating the micro-motion adjusting knob 31' to coincide the focus f of the objective 14 with the position u1.

This is for the reason that an upward and downward micro-motion distance of the front lens 15 is maximum 10 mm and therefore if a position on which an image of an operated part is focused is biased largely from a normal state, it is not able to view the part in a focused state.

So, as shown in FIG. 11, for example, the objective 14 is moved upwardly by lifting up the arm 3 to accord substantially the anterior focus position u0 of the objective 14 with the position u2 on which the image of the portion 8b of the vitreous body is formed.

As a result, since the holding arm 22 for the front lens 15 is lifted up integrally with the objective 14 in the microscope as shown in FIG. 5, a distance from the cornea C of the operated eye 8 to the front lens 15 varies.

Therefore, the micro-motion adjusting screw 31 is adjusted to become a distance H1 from the apex of the cornea C of the operated eye 8 to the front lens 15.

However, since a range capable of adjusting micro-motion of the front lens 15 is limited, it is not able to view the operated part of the vitreous body in a focused state in the microscope for operation as shown in FIG. 5.

Figure 13:
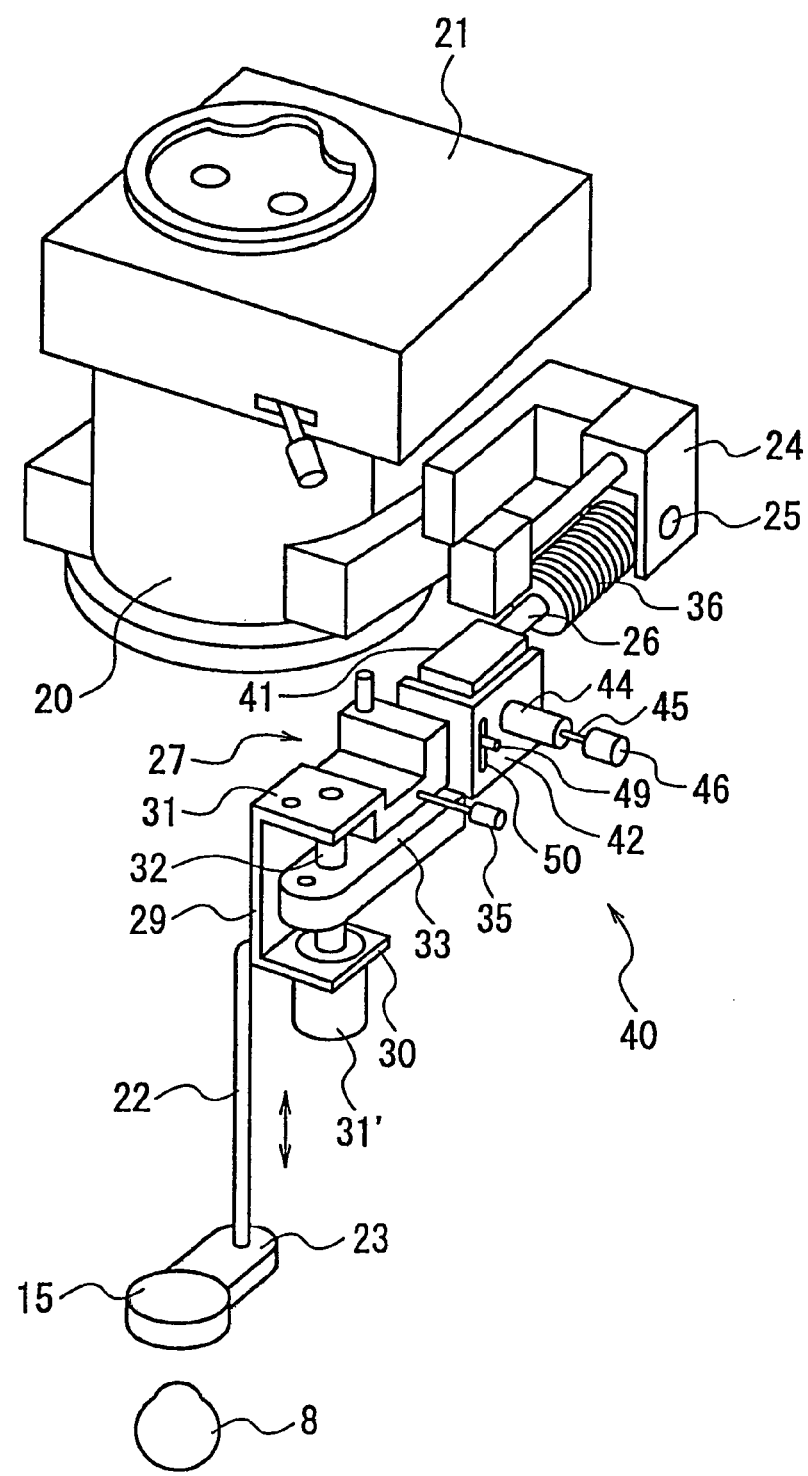
FIG. 13 is a perspective view showing one example of a rough-motion mechanism provided on the objective body tube in the microscope as shown in FIG. 5 to observe the part as shown in FIG. 11.

So, a rough-motion mechanism 40 for upwardly and downwardly moving roughly the holding arm 22 is provided as shown in FIG. 13. The rough-motion mechanism 40 has a rectangular block 41 and a slide plate 42 which is slidably mounted on the rectangular block 41. The rectangular block 41 is provided with positioning concavities 43 which are disposed upward and downward with spaces of 10 mm therebetween as shown in FIG. 14.

The slide plate 42 is formed with a holding cylinder 44 which is provided with a positioning rod 45 which has at the head portion thereof a gripping portion 46, and a flange portion 47.

A biasing spring 48 is provided between the flange portion 47 and an upper portion of the holding cylinder 44. The positioning rod 45 is moved by the biasing spring 48 to energize in a direction of contacting the leading end of the positioning rod with the rectangular block 41. The supporting bracket 27 is mounted on the slide plate 42.

Figure 14:
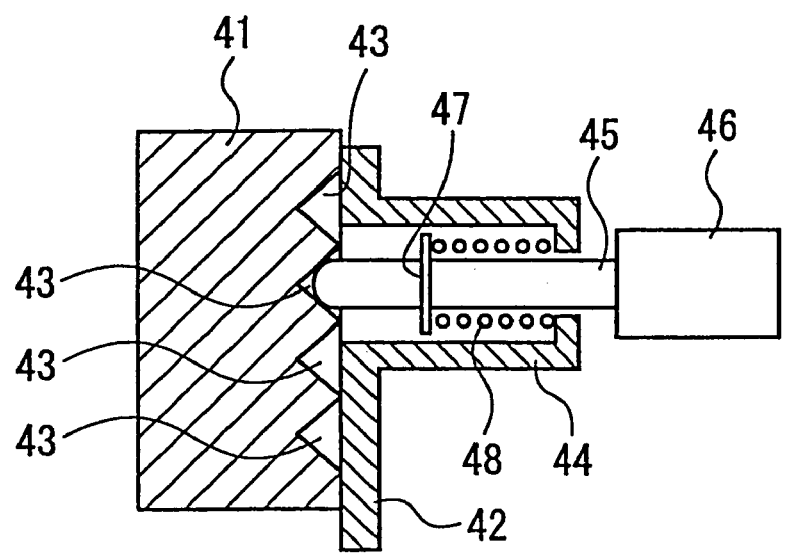
FIG. 14 is a sectional view showing a relationship of a rectangular block and a slide plate in the rough-motion mechanism as shown in FIG. 13.

FIG. 14 shows a state in which the positioning rod 45 is inserted into one of the positioning concavities 43 which is in a reference position. The positioning rod 45 is movable upwardly 10 mm and downwardly 20 mm in the embodiment. Note that in FIG. 13, reference numeral 49 denotes an antislipping pin which is provided on the rectangular block 41 to stop the slip down of the supporting bracket 27, and reference numeral 50 denotes a guide groove for guiding upwardly and downwardly the anti-slipping pin 49.

As shown in FIG. 11, for example, if the portion 8b of the vitreous body of the operated eye 8 is observed, the anterior focus position u0 of the objective 14 is changed from the position u1 to the position u2. The distance of the front lens 15 relative to the cornea C is, then, changed with being moved upwardly by a changed amount of distance from the position u1 to the position u2.

Under the circumferences, the holding arm 22 is moved downwardly by a changed amount of positions between the front lens 15 and operated eye 8 with pulling the gripping portion 46 of the rough-motion mechanism 40 to return the position relationship between the cornea C and front lens 15 to the original state.

Thereafter, the micro-motion adjusting knob 31' is operated to focus on the portion 8b of the vitreous body.

As described above, if the rough-motion mechanism 40 is used, it is able to observe even a part within a range which can not be observed, namely, the neighborhood of the crystalline lens 12 from the retina 8b of the fundus throughout a wide range arriving on the neighborhood of the cornea C.

In this modification, although the rough-motion mechanism 40 is manually operated, the slide plate 42 may be automatically driven to compensate the changed amount of distance of the front lens 15 relative to the operated eye 8 according to upward and downward movement of the objective 14 by use of a driving mechanism for the slide plate 42 and a linear scale provided on the rectangular block 41.

Embodiment 2

Figure 15:
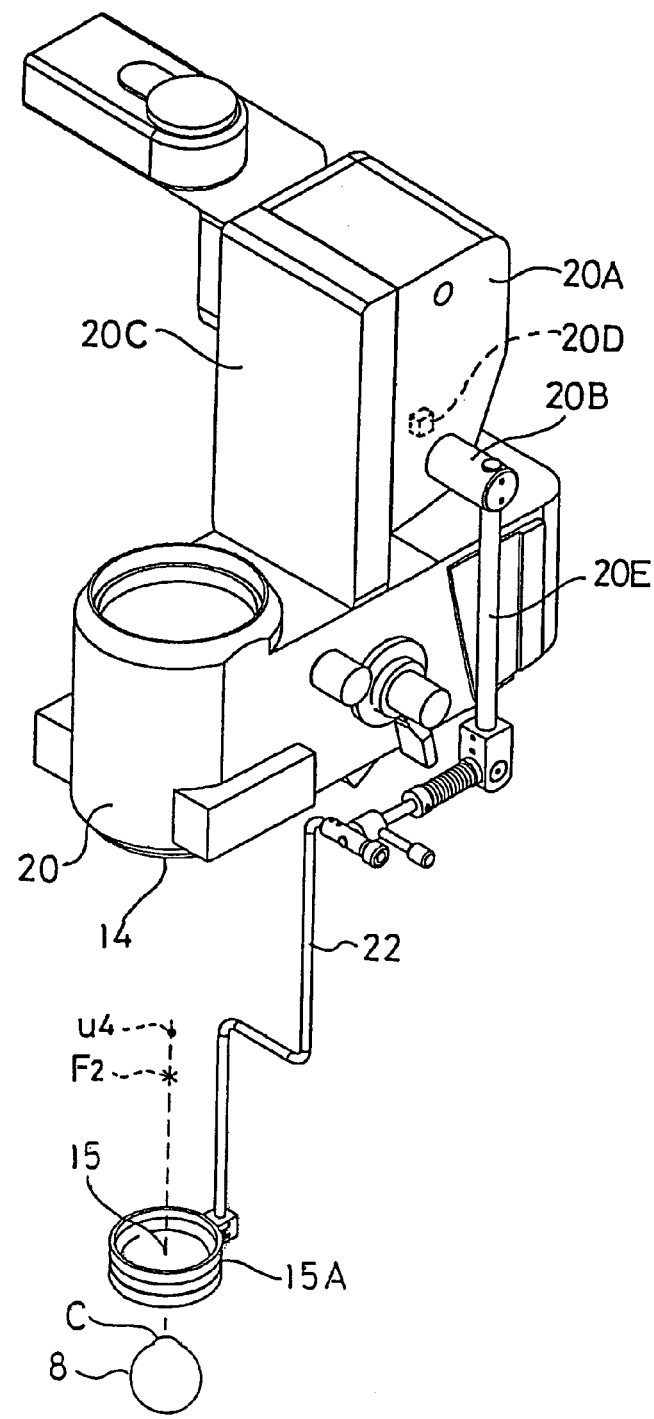
FIG. 15 is a perspective view showing a configuration of the objective body tube according to an embodiment 2.

FIG. 15 shows a configuration in which the objective body tube 20 is micro-motioned upwardly and downwardly relative to an upward and downward micro-motion body portion 20A, and provided on the other end portion of the holding arm 22 of the front lens 15 is a rotating base 20B which is mounted rotatably on the body portion 20A.

The body portion 20A holds slidably a slide plate 20C as a slide member which can be moved upwardly and downwardly by a driving mechanism (not shown) which is provided in the body portion 20A. The objective body tube 20 is formed integrally with the slide plate 20C. Note that the front lens 15 is held by a holding frame 15A.

The aforementioned configuration has the following advantageous effects.

Pupils of incidence of an observing system and of ejection of an illuminating system in the microscope 5 for the operator are positioned adjacent to the objective 14. Images 20A' and 20B' of these pupils are focused on the neighborhood of anterior focus surfaces of the front lens 15 by means of this front lens.

Figure 16A:
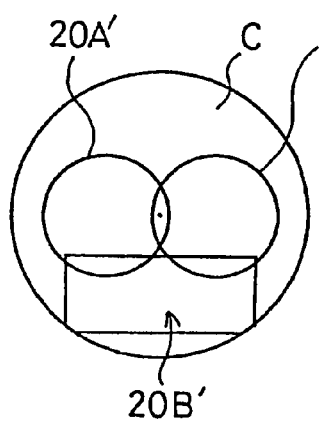
FIG. 16(a) is an explanatory view showing a state of laying to overlap an image of an observed pupil in an observing system with an image of an illuminating pupil in an illuminating system.

Here, when the image 20A' of the incident pupil of the observing system and the image 20B' of the ejection pupil of the illuminating system are overlapped on the cornea C as shown in FIG. 16(a), the illuminating light is diffused on the cornea C and enters into the observing system to cause a glare to occur.

However, the incident and ejection pupils are conjugate with the neighborhood of the cornea C of the eye with respect to the front lens 15.

Figure 16B:
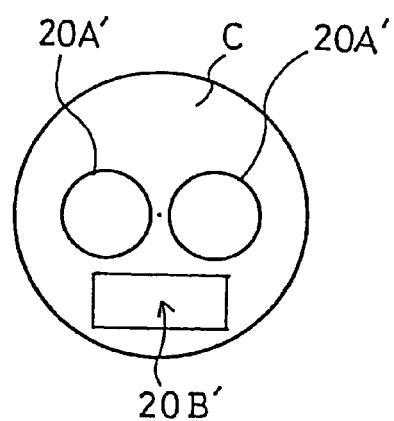
FIG. 16(*b*) is an explanatory view similar to FIG. 16(*a*) showing a state of separating the observing pupil from the illuminating pupil.

That is, if the anterior focus position of the front lens 15 is positioned adjacent to the cornea C, the images 20A' and 20B' is separated on the cornea C to prevent the glare from occurring in the observing system as shown in FIG. 16(b).

By the way, in case of a correct eye, an image of the retina 8a is formed on a focus surface of the posterior focus position F2 of the front lens 15. If the anterior focus position u0 of the objective 14 coincides with the focus surface of the posterior focus position F2, a clear image can be observed by the microscope.

However, in case of a patient with a cataract, there are many cases of removing the crystalline lens 12 of the eye before the vitreous body is operated to enhance visibility of the fundus. When the operated eye 8 from which the vitreous body is removed, the eye becomes a strong far sight.

Figure 17:
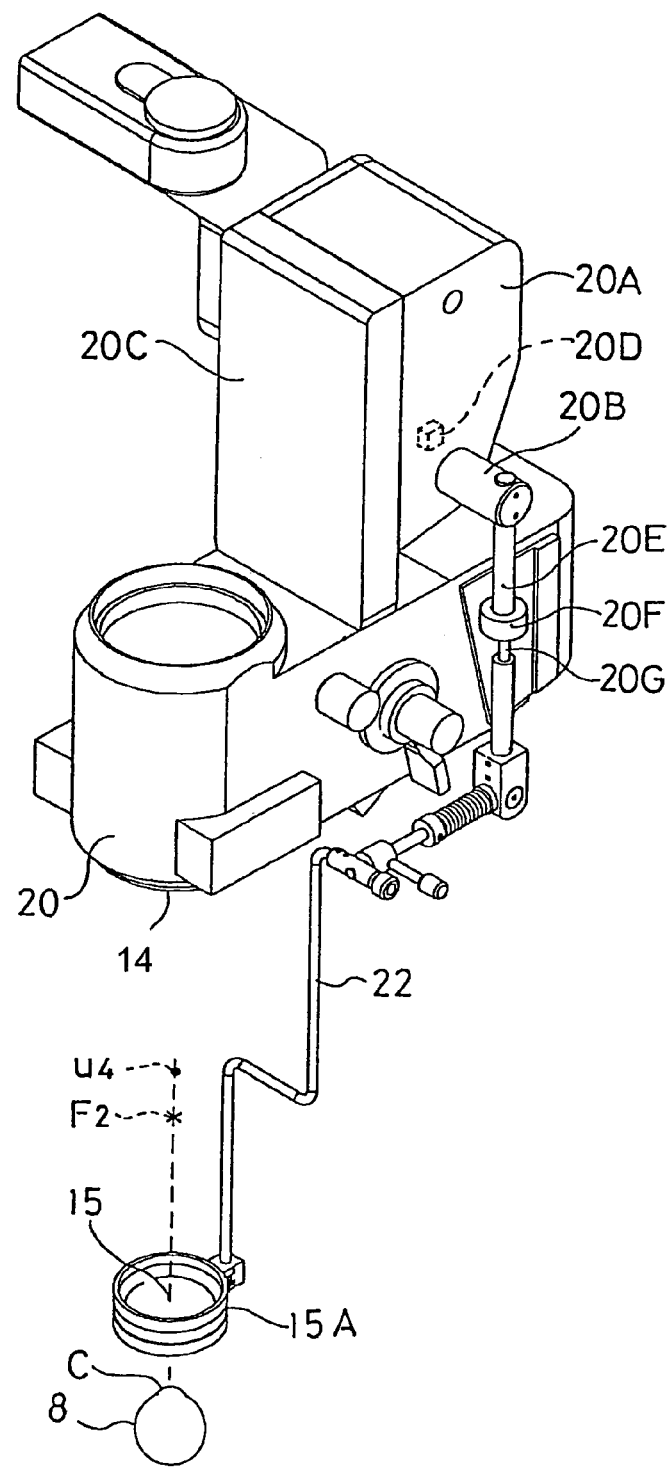
FIG. 17 is a perspective view of the objective body tube showing a configuration in which a linear motor is mounted on a rod arm and the front lens is micro-adjustable as shown in FIG. 15.

In this case, the image of the retina 8a by the front lens 15 is formed in the position u4 close to the objective 14 than the posterior focus position F2 of the front lens 15 as shown in FIG. 17. An observed part is not limited to the fundus, there are many cases for observing the vitreous cavity 13.

If operations of eyes in strong far sight and strong near sight are performed, a conjugate position of an observed object does not become infinity. As described above, when the observed part of the eye is, also, changed, the conjugate position of the observed object does not become infinity. Accordingly, in case of performing such operation, the objective 14 is moved along the optical axis and is again amended to focus according to a position in which the operator wants to observe during the operation.

In this case, if the holding arm 22 is provided on the objective body tube 20, as described above already, as the objective body tube 20 is moved up and down, the front lens 15 is moved up and down together with the objective body tube 20 which moves upwardly and downwardly.

Hence, the position of the front lens 15 relative to the cornea C varies and the images 20A' and 20B' in the incident and ejection pupils, respectively, become out of focus on the cornea C as shown in FIG. 16(a). As a result, the glare is viewed in the microscope when observing it.

However, as shown in the embodiment 2, if the holding arm 22 is mounted rotatably on the body portion 20A, the position of the front lens 15 remains fixed relative to the operated eye 8 even though the objective body tube 20 is moved upwardly and downwardly by operating the foot switch 7.

Accordingly, the separation of the images 20A' and 20B' is held to prevent the glare from entering into the observing system.

A micro-switch 20D for detecting rotation of the rotating base 20B is provided within the body portion 20A as shown at a broken line, and when the objective body tube 20 is moved upwardly and downwardly by turning on the foot switch 7, the front lens 15 is micro-motioned upwardly and downwardly to hold the incident and ejection pupils in the conjugate relationship with the cornea C with respect to the front lens 15.

Namely, a rod arm 20E mounted on the rotating base 20B has two portions as shown in FIG. 17. The rod arm 20E mounts on one thereof a linear motor 20F and on the other thereof an output shaft 20G (a movable body) of the linear motor 20F. When the micro-switch 20D is turned on, the holding arm 22 is micro-motioned by driving the linear motor 20F.

A relationship formula will be described with reference to FIG. 11.

In FIG. 11, if H0 is a focus distance [m] of the objective 14, D is a focus distance [m] of the front lens 15, D' is a refracting power of the eye, a distance from the objective to the front lens 15 is H4', the front lens 15 may be micro-motioned relative to the objective 14 to satisfy the following formula.

$$H1 = D^{-1} + 2 \cdot (D^2 \cdot H_0)^{-1} [1 + \{1 + (4D'/D^2 \cdot H_0)\}^{1/2}]^{-1}$$

$$H4' = H_0 + D^{-1} + D^{-2} \cdot [(H_1 + (1/D')) - (1/D)]$$

With such construction, the images 20A' and 20B' can be separated clearly to prevent the glare from entering into the observing optical system.

Embodiment 3

Figure 18:
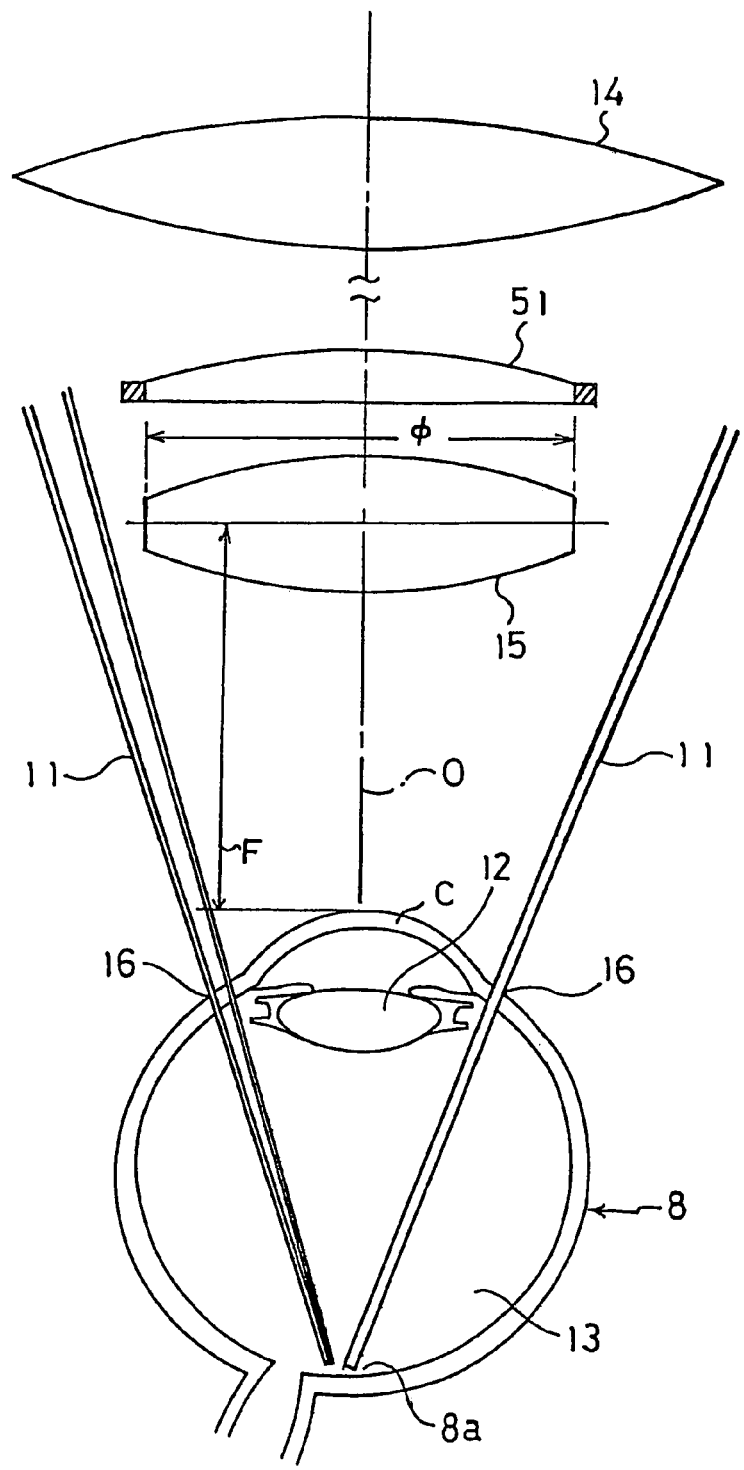
FIG. 18 is a pattern diagram showing a state of inserting a loupe in a front of the front lens in observing an inserting part of an operation instrument in an embodiment 3.

FIG. 18 is an explanatory view showing a positional relationship between the inserting part of the operation instrument 11 and front lens 15.

The operation instrument 11 is inserted into the operated eye 8 after the distance from the apex of the cornea C to the front lens 15 is determined to not occur the glare so that the operator can observe the image of the retina 8a of the fundus.

Figure 19:
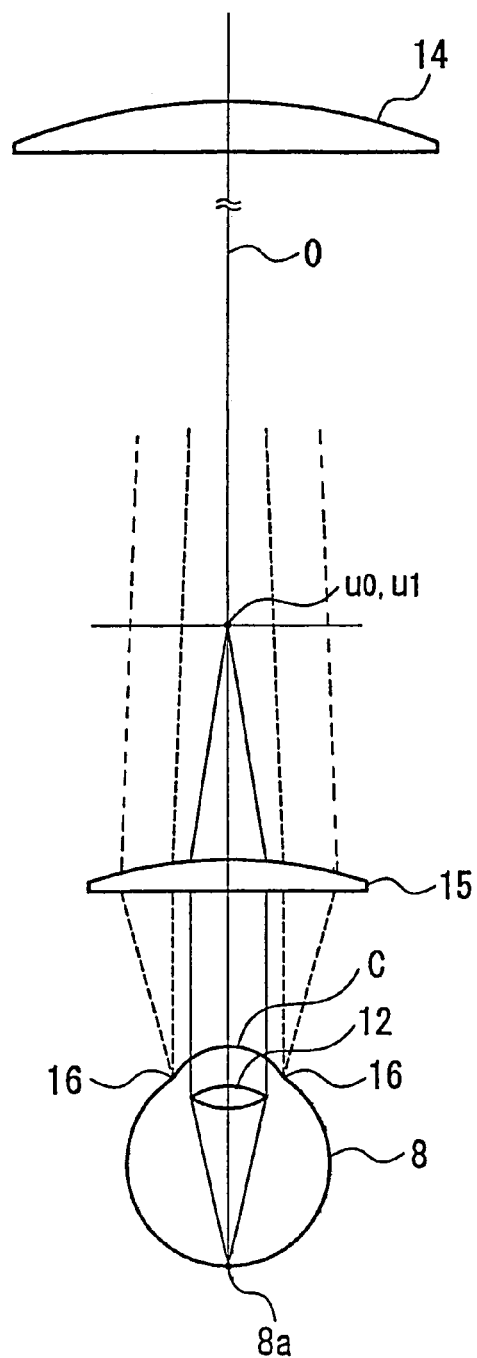
FIG. 19 is a pattern diagram showing a focused position of the inserting part of the operation instrument when no the loupe is inserted and fundus of the operation eye is observed.

As shown in FIG. 19, because the inserting part 16 is positioned closely to the posterior focus surface of the front lens 15, the conjugate point is generally infinity and the image by the objective 14 is not focused. On the other hand, since the anterior focus position u0 coincides with the position u1, the inserting part can not be observed when observing it through the objective 14.

Accordingly, the operator views one or more inserting parts 16 with the operator peeping from the sideward not through the front lens 15 by disengaging the eye with the eyepiece 39. However, it is difficult for the operator performing the operation to disengage repeatedly the eye with the eyepiece 39 in inserting the operation instrument 11 into the eye.

Figure 20:
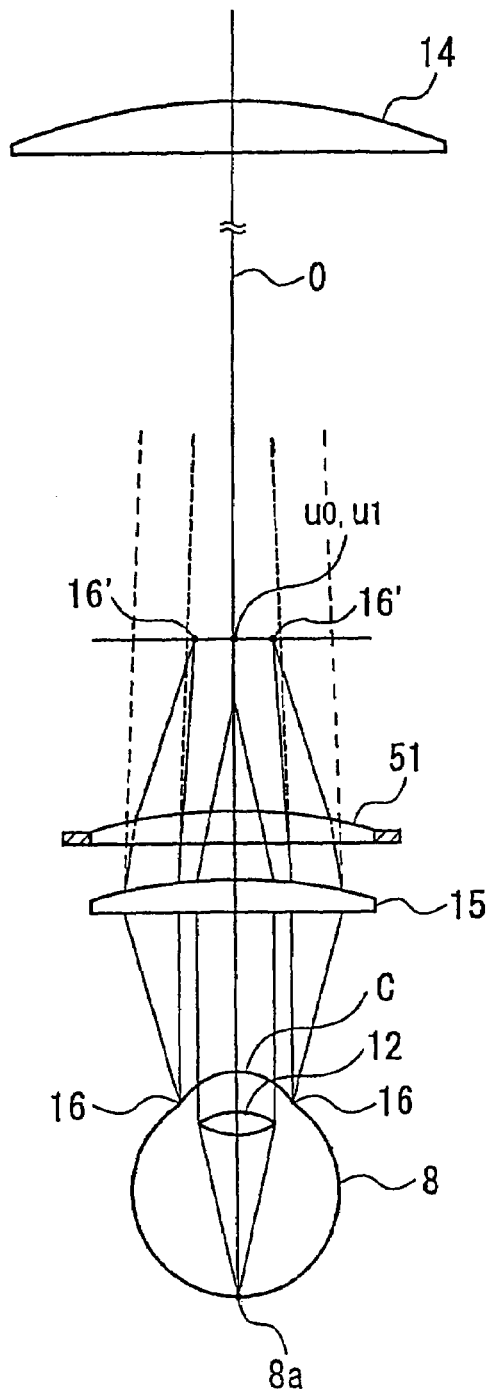
FIG. 20 is a pattern diagram showing a state of coinciding the focused position of the inserting part with the fundus when the fundus is observed and the loupe is inserted.

For example, the operation instrument 11 is inserted in the eye through the inserting part 16 with observing the images of the inserting part to coincide the images with the anterior focus position u0 of the objective 14 by inserting a loupe 51 in the optical path of the observing optical system of the front lens 15 as shown in FIG. 20.

Figure 21:
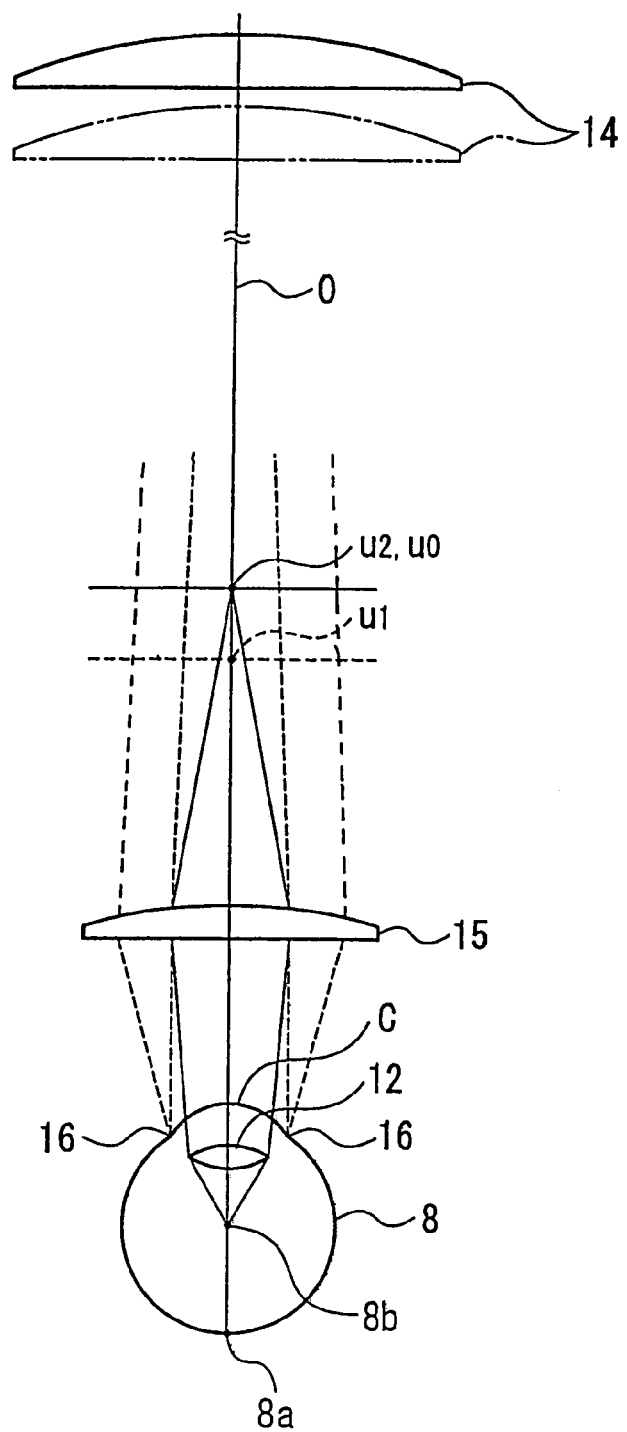
FIG. 21 is a pattern diagram showing a focused position of the inserting part of the operation instrument when vitreous body part is observed and no the loupe is inserted.
Figure 22:
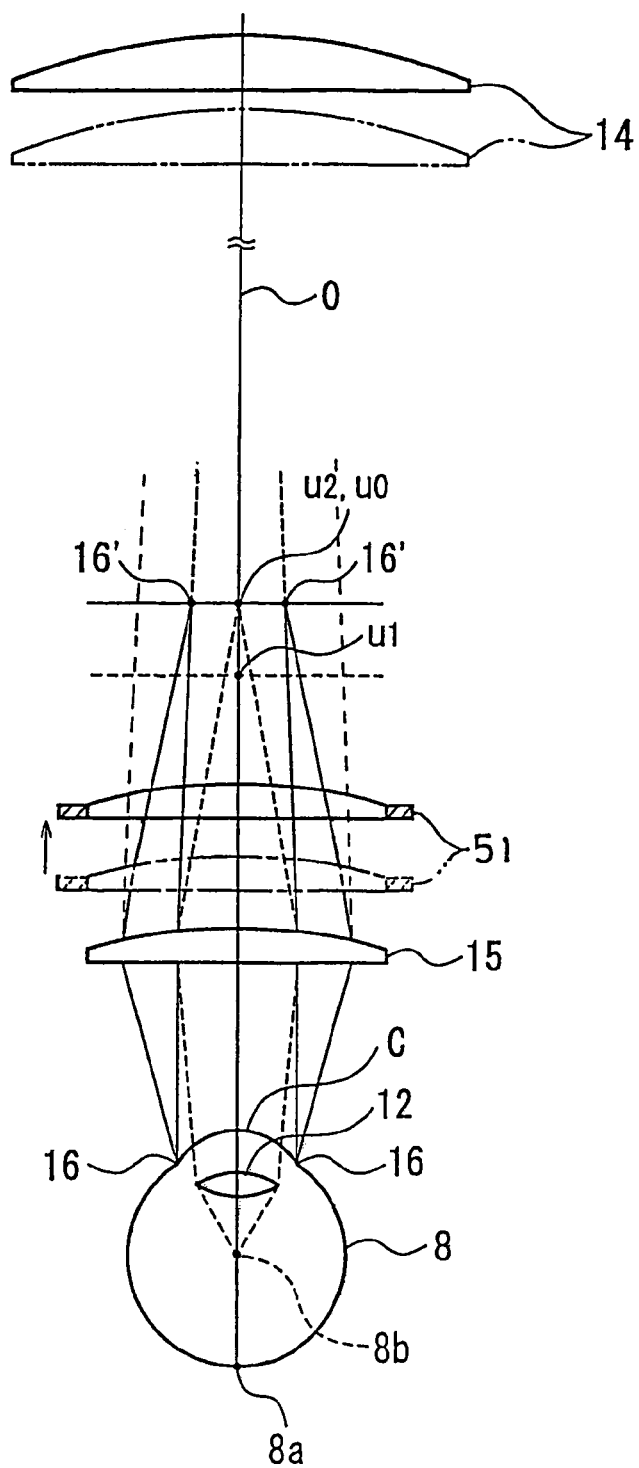
FIG. 22 is a view showing a state of coinciding the focused position of the inserting part of the operation instrument with the vitreous body part when the vitreous body part is observed, no the loupe is inserted and a space between the loupe and front lens is changed.

As shown in FIG. 21, for example, if the part 8b of the vitreous body is operated, the anterior focus position u0 of the objective 14 must be changed from the position u1 to the position u2. However, when the anterior focus position u0 is changed from the position u1 to the position u2, the distance between the loupe 51 and front lens 15 must be changed to form the image 16' of the inserting part 16 on the anterior focus position u0 as shown in FIG. 22.

Figure 23:
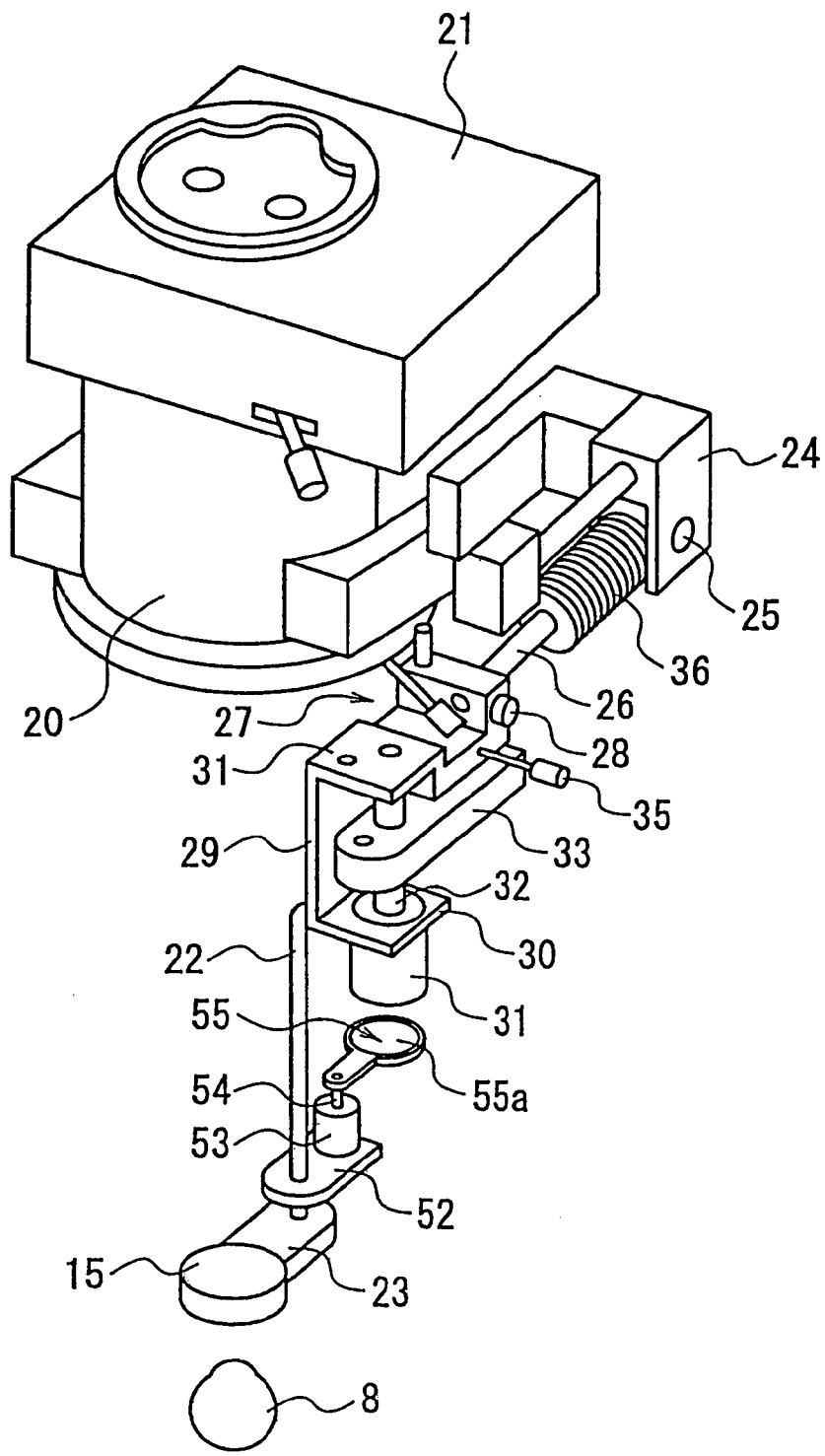
FIG. 23 is a perspective view showing a configuration of the objective body tube according to an embodiment 3.
Figure 24:
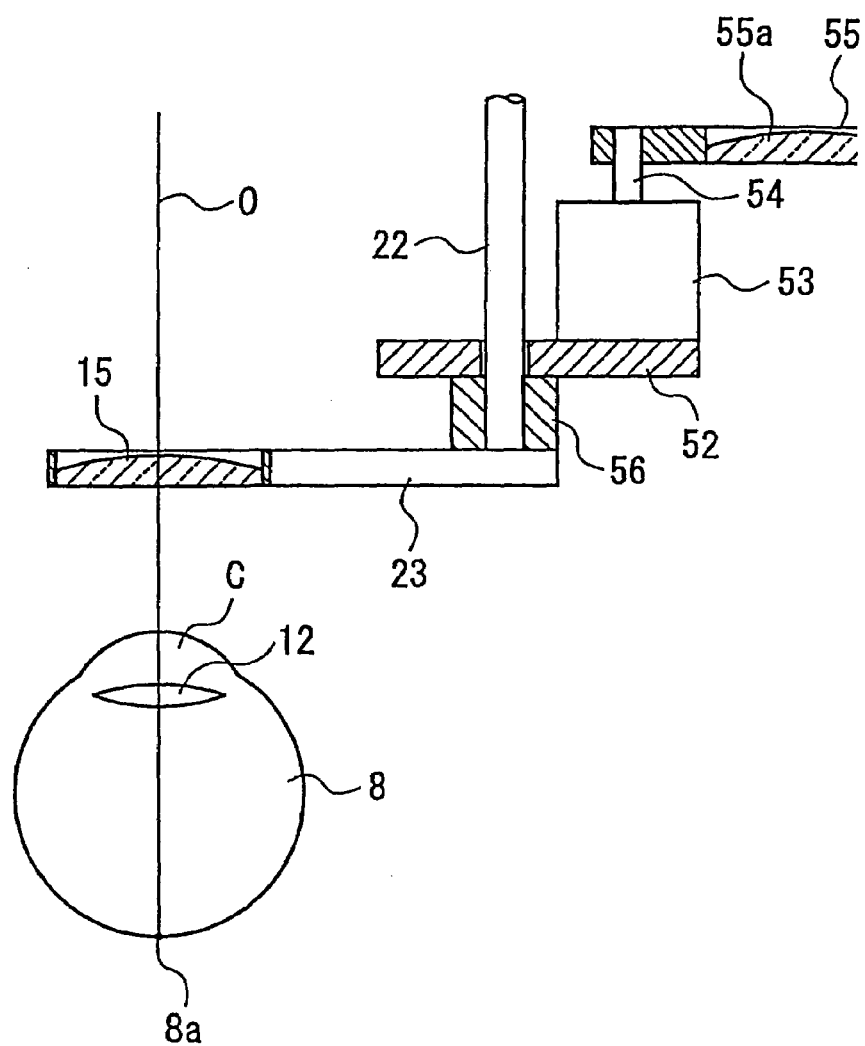
FIG. 24 is a partial enlarged explanatory view of a loupe holding mechanism as shown in FIG. 23.

Therefore, a configuration of providing the loupe holding mechanism on the arm is used as shown FIGS. 23 and 24. The loupe holding mechanism includes a rotated plate 52 mounted rotatably on the holding arm 22, a linear motor 53 provided on the rotated plate 52 and a loupe 55 mounted on an output shaft 54 of the linear motor 53.

Numeral 55a denotes a convex lens of the loupe 55. The linear motor 53 has a function of moving the loupe 55 upwardly and downwardly. A spacer member 56 is provided between the holding plate 23 and the rotated plate 52.

As described above, provision of the rotated plate 52 on the holding arm 22 in inserting the loupe 55 in the optical path of the observing optical system to observe the inserting part 16 causes the loupe 55 to hold in a stable state. Upward and downward movement of the loupe 55 causes the microscope to observe the inserting part 16 in a focus state even though the anterior focus position u0 of the objective 14 is changed.

Embodiment 4

Figure 25:
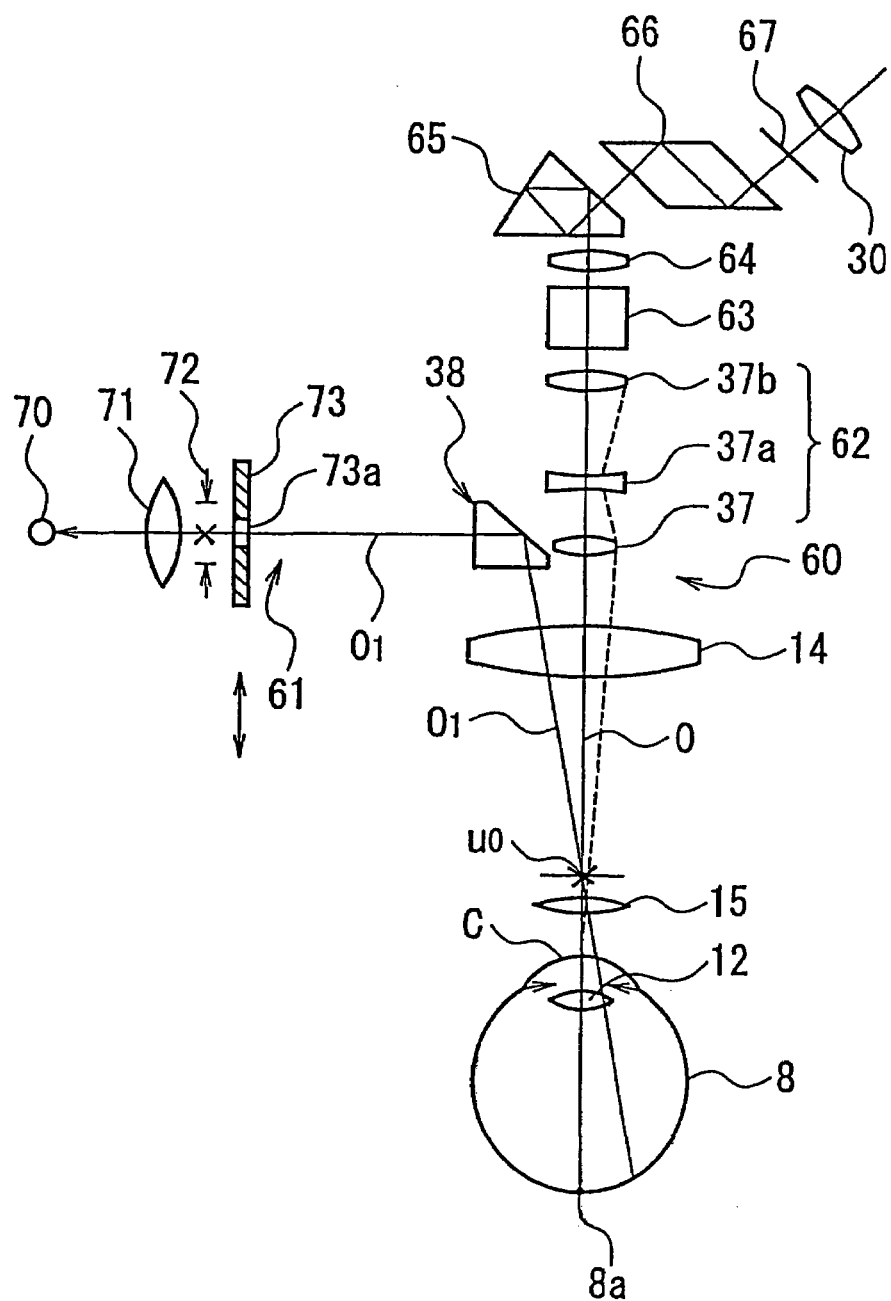
FIG. 25 is a view showing a configuration of an optical system of a microscope for operation according to an embodiment 4.

FIG. 25 shows a whole view of an optical system of the microscope 5 for operation.

In FIG. 25, numeral 60 denotes an observing optical system and numeral 61 an illuminating optical system. As one example, a pair of observing optical systems 60 are disposed at the opposite sides of an optical axis O of the objective 14. Each of the observing optical systems 60 comprises a zoom lens system 62, a beam splitter 63, a focused image lens 64, an erect image prism 65, an eye width adjusting prism 66, and a scope diaphragm 67 (see FIG. 25). The zoom lens system 62 includes zoom lenses 37, 37a and 37b.

The illuminating optical system 61 comprises an illuminating light source 70, a condenser lens 71, illuminating field diaphragm 72 and a slit plate 73. The slit plate 73 has a slit hole 73a. The slit plate 73 is disposed to move in and out of an illuminating optical path of the illuminating optical system 61 and is movable vertically to an illuminating optical axis O1 when the slit plate is inserted in the illuminating optical path.

Figure 29:
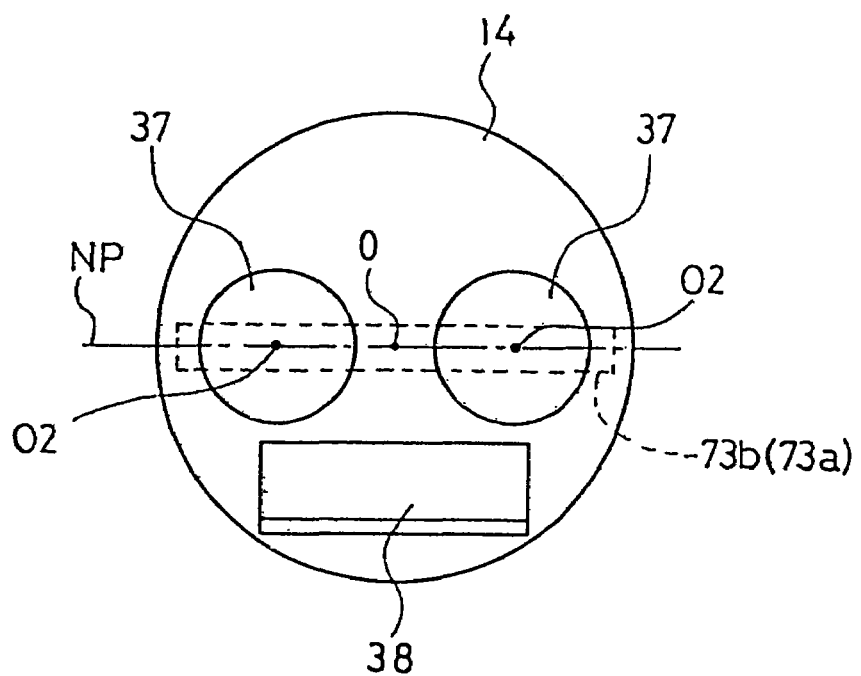
FIG. 29 is an explanatory view showing a positional relationship of a projected image of a slit hole and both axes of a pair of observing optical systems.

The slit hole 73a extends in a direction vertical to the illuminating optical axis O1 and the moving direction of the slit plate 73 (see FIG. 25) and in a parallel direction to a plane NP in which an image 73b (namely, slit illuminating light P3, see FIG. 29) of the slit hole 73a projected on the fundus as shown in FIG. 29. The image 73b is shown with a broken line in FIG. 29 for the reason that it is focused on the fundus.

The illuminating field diaphragm 72 is conjugate with the anterior focus position u0 which is conjugate with the retina 8a of the fundus in the embodiment.

A reason of providing the slit plate 73 in the illuminating optical system 61 is as follows.

Figure 26:
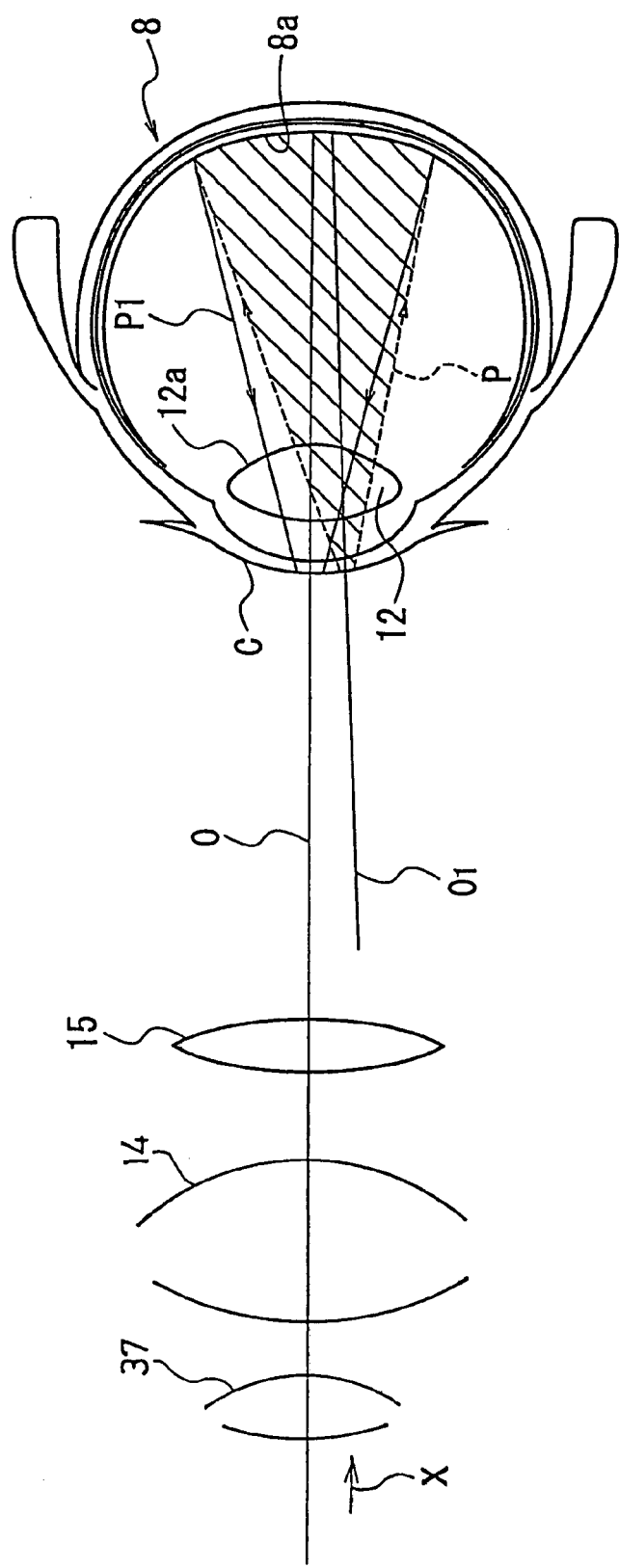
FIG. 26 is a longitudinal sectional view of the operated eye showing a state in which bio-liquid is filled in the eye.

The illuminating light P is guided to the fundus of the operated eye 8 through the front lens 15, cornea C, crystalline lens 12 to illuminate the fundus as shown in FIG. 26. Light P1 reflected on the fundus is guided to the front lens 15 through the crystalline lens 12 and cornea C and then is focused in air on the anterior focus position u0 of the objective 14 through the front lens 15.

As shown in FIG. 26, if the vitreous body is filled with the bio-liquid, since a difference of refractive index of a boundary surface between the vitreous body 12 and bio-liquid is less, reflected index of the light P on the back surface 12a of the vitreous body is less and therefore a ratio that scattered reflected light on the back surface 12a enters in the optical path of the observing optical system is less as shown in FIG. 26.

Figure 27:
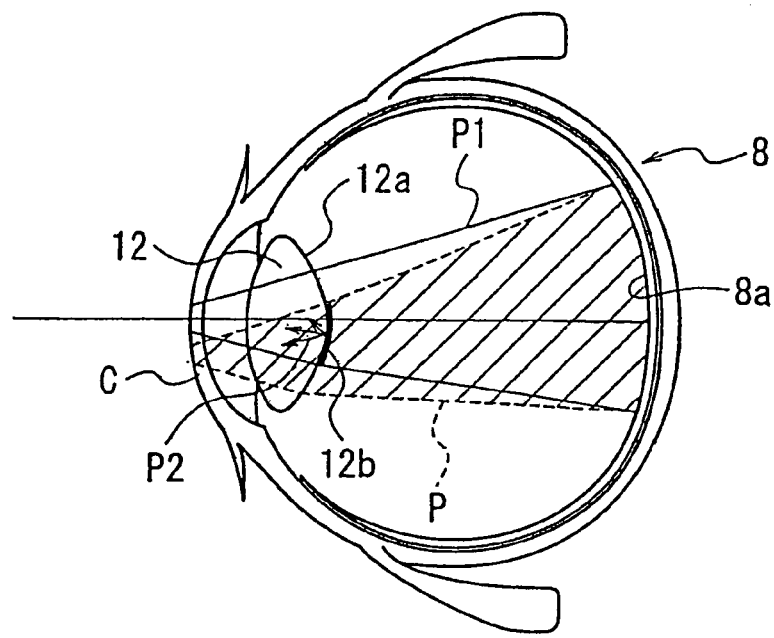
FIG. 27 is a longitudinal sectional view of the operated eye showing a state in which the vitreous body is removed and air is filled in the eye.

However, as shown in FIG. 27, if the vitreous body is removed and the interior of the operated eye 8 is filled with gas or air, a part 12b of the back surface 12a of the vitreous body which scatters the illuminating light P is in a portion of the optical path of the reflected light P1 on the fundus. Accordingly, because a portion of the scattered reflected light P2 on the part 12b enters in the optical path of the observing optical system 60, a glare occurs when observing the fundus through the eyepiece 39. So, as shown in FIG. 28, slit illuminating light P3 may be used to illuminate the fundus through the cornea C and crystalline lens 12 by inserting the slit plate 73 in the optical path of the illuminating optical system 61.

With such construction, the part 12b which receives scattering of the slit illuminating light P3 on the back surface 12a of the crystalline lens 12 is separated from a part 12c through which the reflected light P1 on the fundus to not occur in the observing optical path the glare resulting from the scattered reflected light P2 the back surface 12a of the crystalline lens 12.

Figure 28:
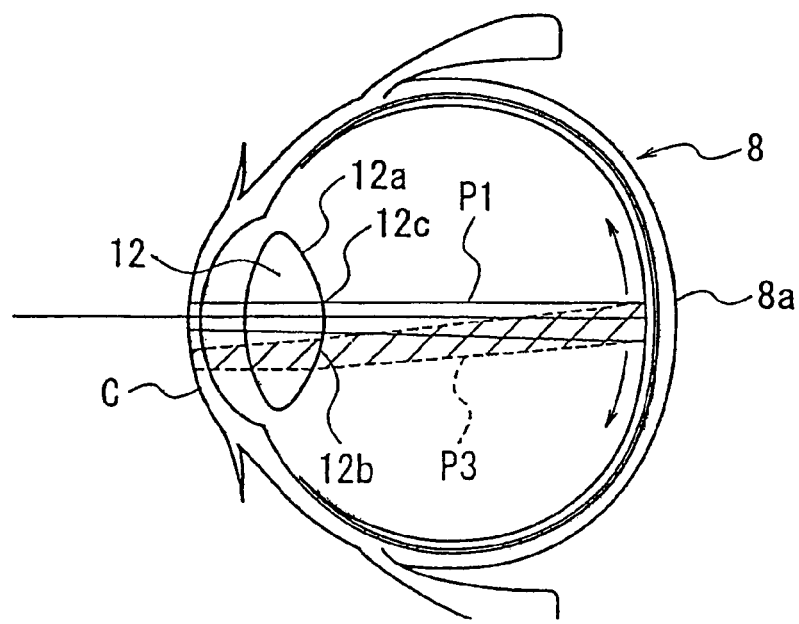
FIG. 28 is a longitudinal sectional view of the operated eye showing a state in which the fundus of the operated eye is illuminated with slit illuminating light.

Further, as shown in FIG. 25, when the slit plate 73 is moved vertically to the illuminating optical axis O1, slit light moves in a direction as shown in arrow in FIG. 28 to enable observe the entire of the fundus 8a.

As shown in FIG. 29, when the slit plate 73 is moves vertically to the illuminating optical axis O1, the projected image 73b (slit illuminating light P3) of the slit hole 73a formed on the fundus 8a is moved to approach to and separate from the optical axis O of the objective 14 with holding the parallel relationship with the surface NP as shown at a broken line. Here, the reason that the projected image 73b is illustrated at the broken line is for showing a relationship between the positions of the projected image 8b and zoom lens 37 if the projected image 8b may be viewed on the fundus 8a through the objective 14.

Embodiment 5

Figure 30:
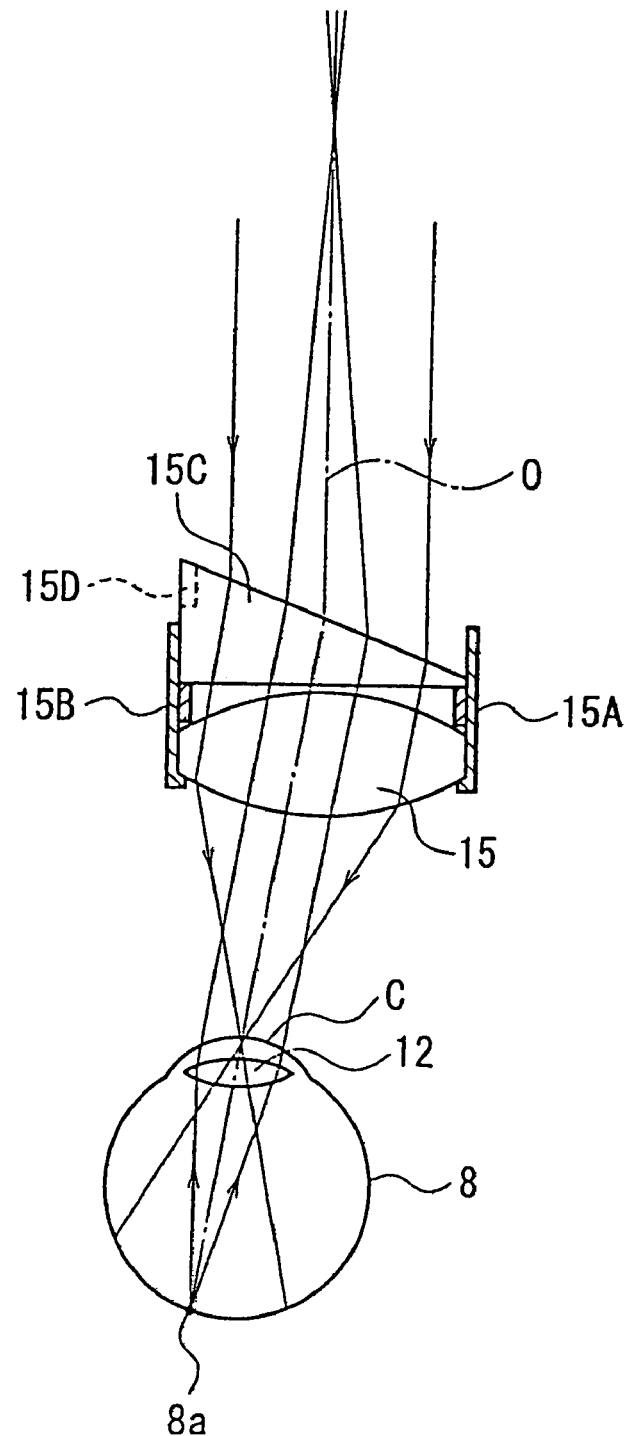
FIG. 30 is a sectional view showing a configuration of a front lens portion according to an embodiment 5.

FIG. 30 shows a modification of the holding frame 15A of the front lens 15. In the embodiment, an inner cylinder 15B is inserted into the holding frame 15A of the front lens 15. A prism 15C can be mounted removably on the inner cylinder 15B. The prism 15C is used to observe a peripheral portion of the retina 8a by refracting the optical axis. A bottom portion of the prism 15C is formed with an engaging groove 15D in which the leading ends of tweezers as the operation instrument 11 are inserted to rotate the prism 15C thus enabling observation of the peripheral portion of the fundus.

It is desirable that since an observing angle of field by the front lens has about 40 degrees, an angle of deviation by the prism 15C is a range of about 10 to 20 degrees.

When a diameter of pupil of an eye of a patient is less, observing and illuminating beams intend to be interrupt by the pupil. In order to avoid this, it is preferable to take a configuration of providing a device which minimizes optically a space between the observing and illuminating pupils in the microscope for operation.

It is applicable to perform an operation having the operation instruments at both hands with illuminating the interior of the operated eye by a microscope illuminating device by use of the front lens arranged in a front of the operated eye.

It should be noted that although some embodiments of the present invention have been described, present invention is not limited to the embodiments above and that various changes and modifications my be made without departing from the spirit of the invention.

The invention claimed is:

1. A microscope for operation comprising:
    an objective body tube for holding an objective;
    a front lens disposed between an eye to be operated upon and an anterior focus position of the objective;
    a zoom lens provided in the objective body tube;
    a slide member for causing said objective body tube to slide along an optical axis of the objective;
    a body portion for holding slidably said slide member; and
    a holding arm rotatably mounted on said body portion at one end portion of the holding arm and configured for holding the front lens at a second end portion of the holding arm, to move the front lens in and out of the optical axis of the objective,
    wherein a position of the front lens remains fixed relative to the eye to be operated upon, regardless of sliding of the objective body tube from a position to another position.

2. The microscope for operation according to claim 1, wherein said front lens is micro-motionable upwardly and downwardly along the optical axis.

3. The microscope for operation according to claim 1, which further comprises a prism provided rotatably on said holding ann for observing a peripheral portion of the fundus of said eye.

* * * * *